(12) United States Patent
Hiller et al.

(10) Patent No.: US 10,080,676 B2
(45) Date of Patent: Sep. 25, 2018

(54) DELIVERY DEVICES AND RELATED METHODS OF USE

(71) Applicant: Boston Scientific Scimed, Inc., Maple Grove, MN (US)

(72) Inventors: Jeri'Ann Hiller, Westford, MA (US); Sandra Nagale, Westford, MA (US); John W. Sheets, Jr., Edina, MN (US); Mark W. Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 530 days.

(21) Appl. No.: 14/211,440

(22) Filed: Mar. 14, 2014

(65) Prior Publication Data

US 2014/0276590 A1  Sep. 18, 2014

Related U.S. Application Data

(60) Provisional application No. 61/829,348, filed on May 31, 2013, provisional application No. 61/798,618,
(Continued)

(51) Int. Cl.
*A61M 31/00* (2006.01)
*A61F 5/00* (2006.01)

(52) U.S. Cl.
CPC .......... *A61F 5/0076* (2013.01); *A61F 5/0069* (2013.01)

(58) Field of Classification Search
CPC ........ A61F 5/00; A61F 5/0076; A61F 5/0069; A61M 25/10; A61M 25/0074;
(Continued)

(56) References Cited

U.S. PATENT DOCUMENTS 6,692,490 B1  2/2004  Edwards
2003/0171645 A1*  9/2003  Silverman ........ A61B 17/12031
600/29
(Continued)

FOREIGN PATENT DOCUMENTS

WO  WO 2012/083155 A2  6/2012
WO  WO 2012083155 A2 *  6/2012  ............ A61M 25/10
WO  WO 2013/039711 A2  3/2013

OTHER PUBLICATIONS

"Core Technology," retrieved from Contura website at http://www.contura.com/produsts/core-technology on Dec. 28, 2012 (2 pages).
(Continued)

*Primary Examiner* — Kevin C Sirmons
*Assistant Examiner* — Tiffany Legette-Thompson
(74) *Attorney, Agent, or Firm* — Bookoff McAndrews, PLLC

(57) ABSTRACT

According to an aspect of the disclosure, a treatment method may include treating a wall of a portion of a gastrointestinal tract of a patient. Treating the wall may include positioning one or more injection units adjacent to the wall. Treating the wall may also include affecting at least one of movement of gastrointestinal tract contents through the gastrointestinal tract and absorption of gastrointestinal tract contents by the gastrointestinal tract, by injecting material into the wall using the one or more injection units. Injecting the material may include injecting the material between layers forming at least a portion of the wall.

10 Claims, 26 Drawing Sheets

Related U.S. Application Data filed on Mar. 15, 2013, provisional application No. 61/799,260, filed on Mar. 15, 2013.

(58) Field of Classification Search
CPC .......... A61M 25/1002; A61M 25/0084; A61M 2025/1013; A61M 2025/0087; A61M 2025/1086; A61M 2025/105; A61M 2025/0086; A61M 2025/1011
USPC ............... 604/103.1, 104, 506, 516; 606/192
See application file for complete search history.

(56) References Cited

U.S. PATENT DOCUMENTS

| | | | |
|---|---|---|---|
| 2006/0190022 A1* | 8/2006 | Beyar | A61F 2/958 606/192 |
| 2006/0247720 A1* | 11/2006 | Starkebaum | A61N 1/36007 607/40 |
| 2007/0282184 A1 | 12/2007 | Roberts | |
| 2008/0125709 A1 | 5/2008 | Chang et al. | |
| 2009/0012469 A1* | 1/2009 | Nita | 604/104 |
| 2010/0152704 A1 | 6/2010 | Lee et al. | |
| 2010/0198139 A1 | 8/2010 | Glickman | |
| 2010/0256594 A1 | 10/2010 | Kimmell et al. | |
| 2010/0268191 A1* | 10/2010 | Trudel | A61K 9/5005 604/509 |
| 2011/0166516 A1 | 7/2011 | Orr | |
| 2013/0018281 A1 | 1/2013 | Nagale et al. | |
| 2013/0072855 A1 | 3/2013 | Sherry et al. | |
| 2013/0090640 A1 | 4/2013 | Nagale et al. | |
| 2013/0090648 A1 | 4/2013 | Nagale et al. | |

OTHER PUBLICATIONS

Hillel, Alexander T. et al., "Photoactivated Composite Biomaterial for Soft Tissue Restoration in Rodents and in Humans," Science Translation Medicine, vol. 3, Iss. 93, p. 93ra67 (2011) (13 pages).

Karajanagi, Sandeep S. et al., "Assessment of Canine Vocal Fold Function After Injection of a New Biomaterial Designed to Treat Phonatory Mucosal Scarring," Annals of Otology, Rhinology & Laryngology, vol. 120, pp. 175-184 (2011), Abstract (1 page).

"Products: Tissue Repair," retrieved from Fidia website at http://www.fidlapharma.com/files/index.cfm?id_rst=137 on Dec. 28, 2012 (3 pages).

"Treatment of morbid obesity by intraparietogastric administration of botulinum toxin: a randomized, double-blind, controlled study" Internationl Journal of Obesity (2007) 31, 707-712 (6 pages).

"Alerations of Gastrointestinal Motility in Obesity" Obesity Research vol. 12 No. 11 Nov. 2004 1723-1732 (10 pages).

* cited by examiner

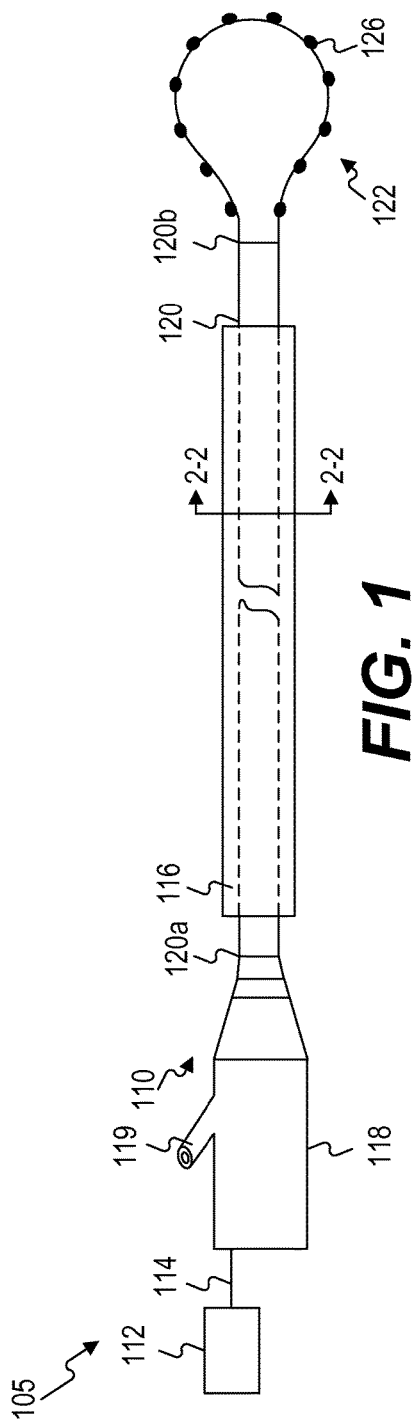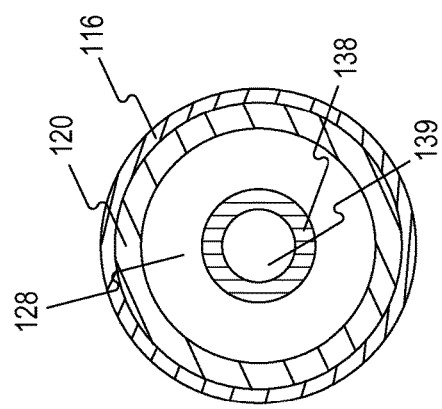

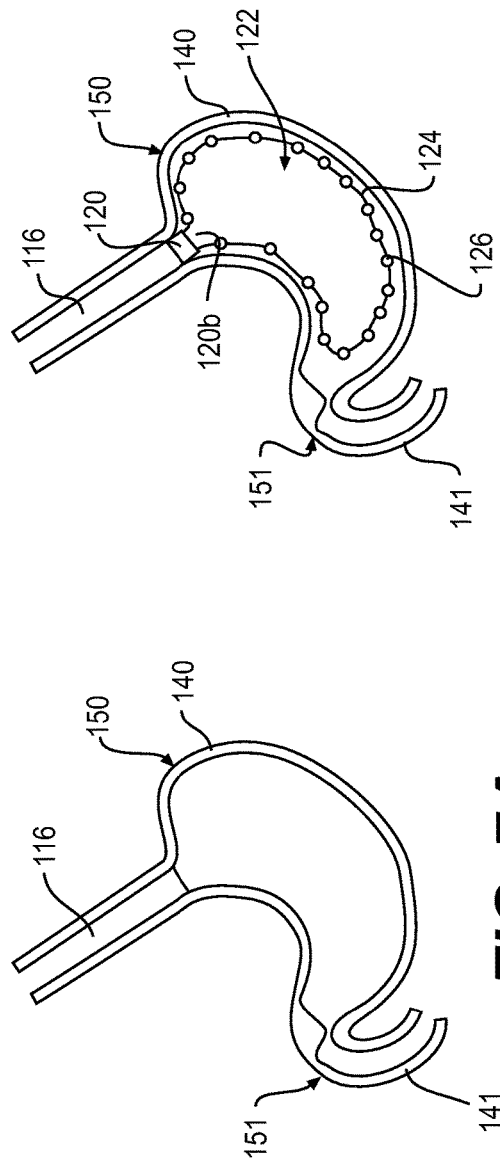
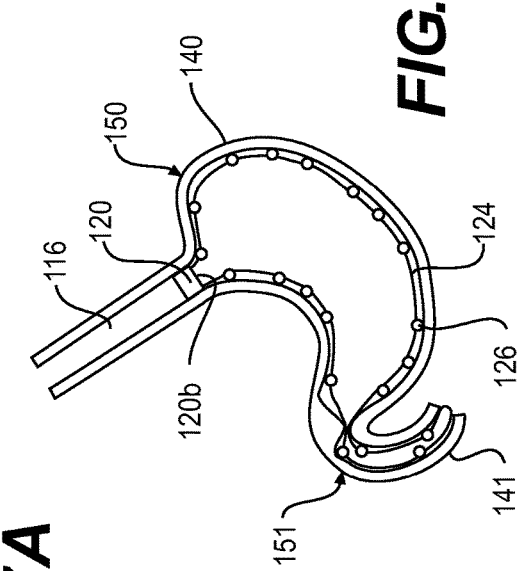
FIG. 7A
FIG. 7B
FIG. 7C

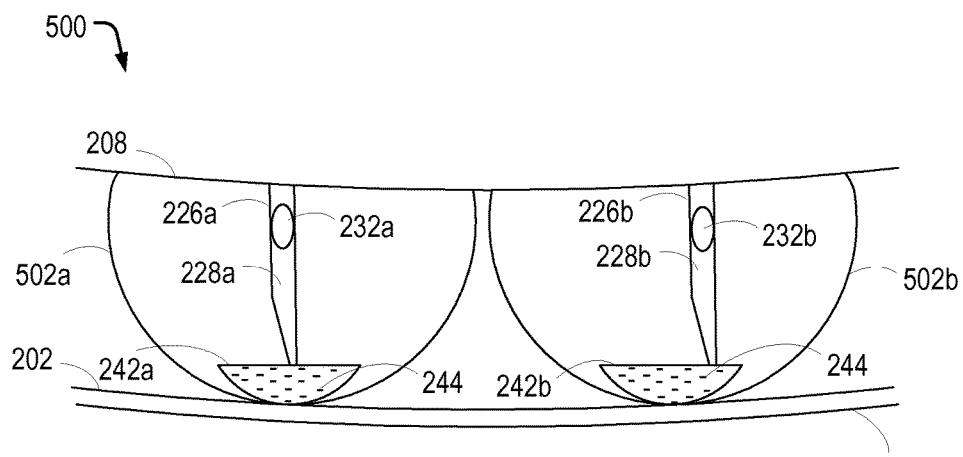
FIG. 10A
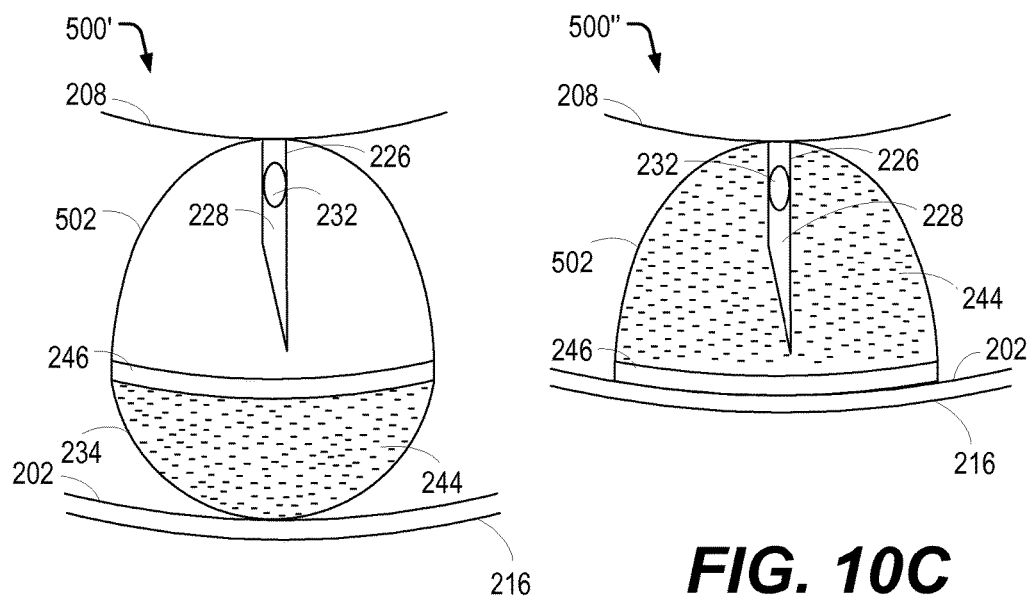
FIG. 10B
FIG. 10C

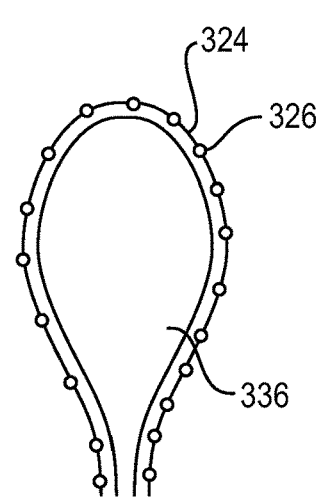 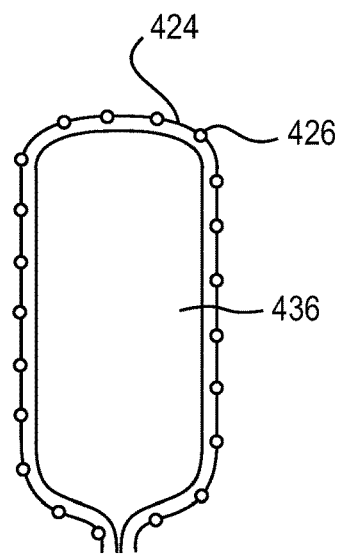
FIG. 13A  FIG. 13B
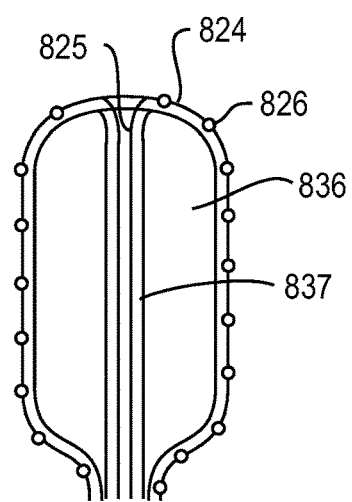 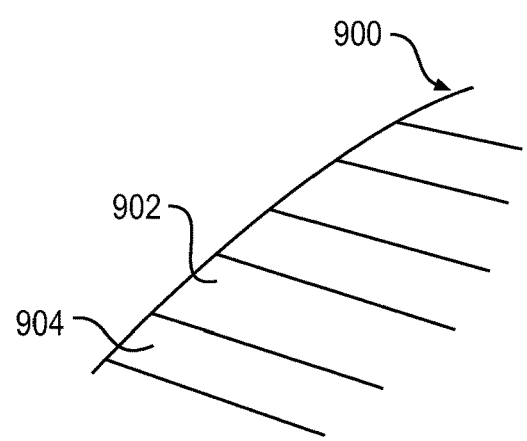
FIG. 13C  FIG. 13D

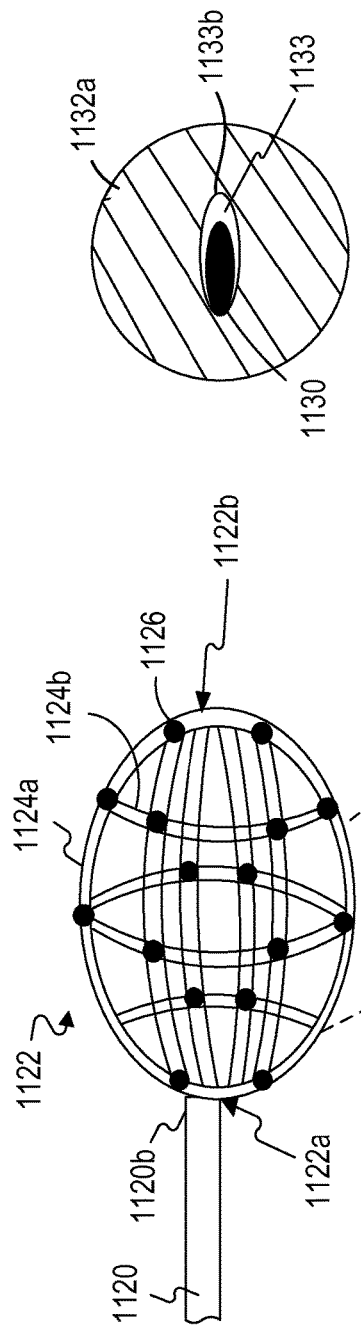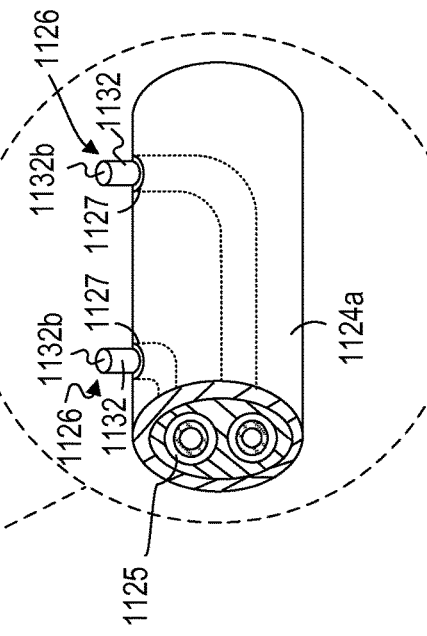
FIG. 16
FIG. 17
FIG. 18

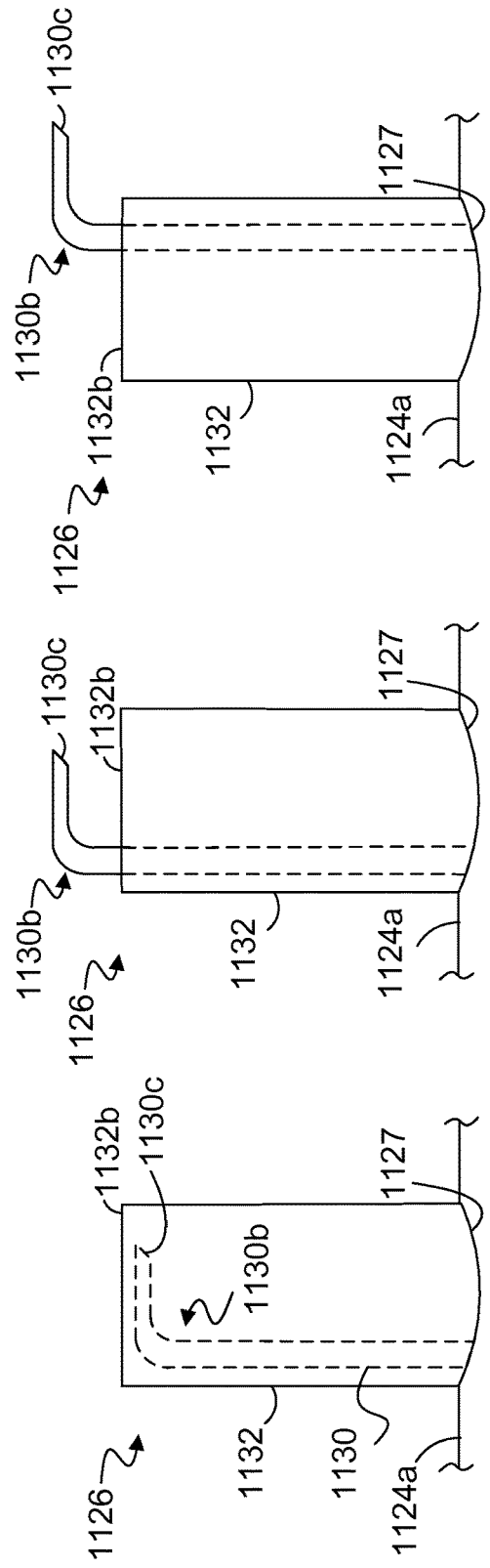

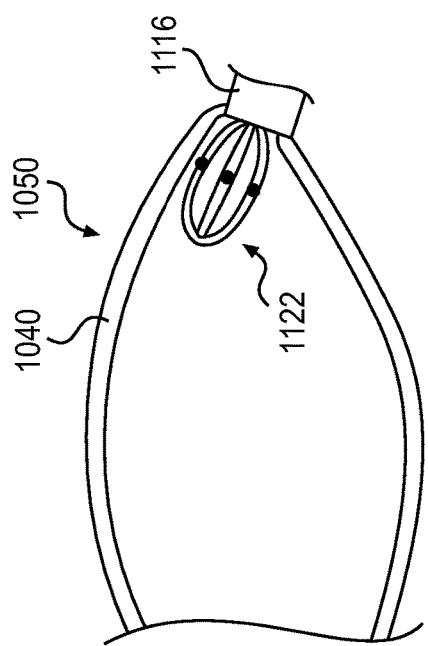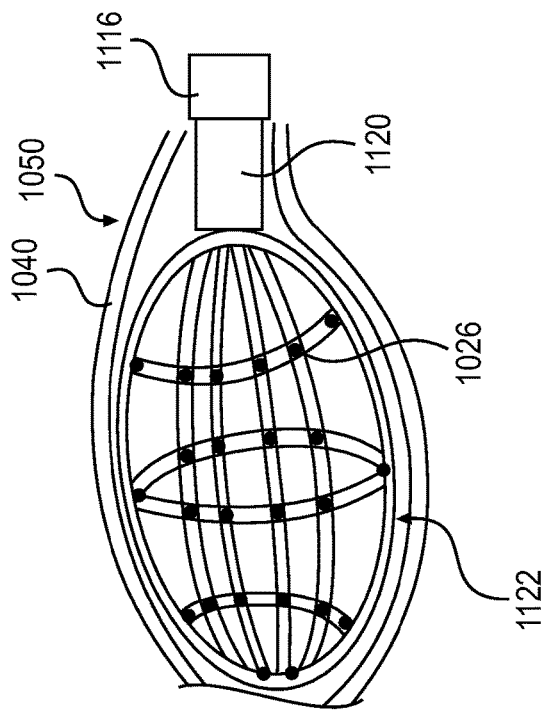

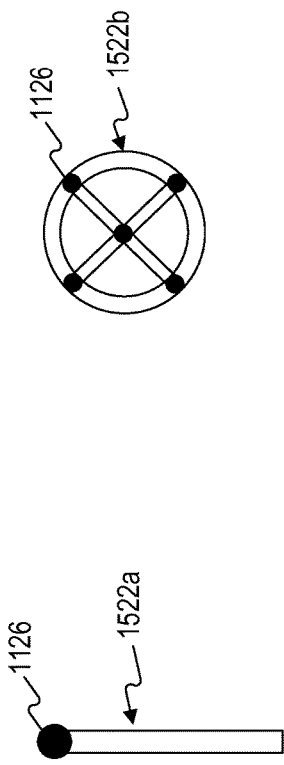
FIG. 22A
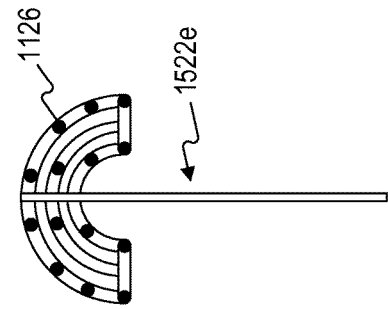
FIG. 22B
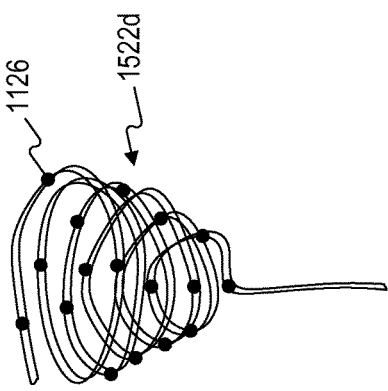
FIG. 22D
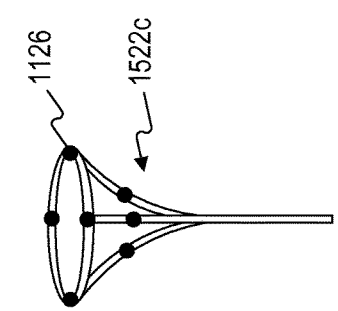
FIG. 22C
FIG. 22E

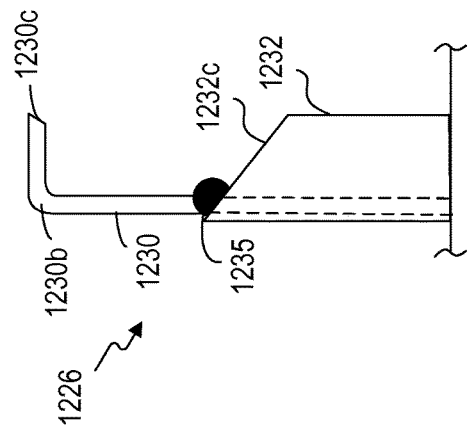
FIG. 23A
FIG. 23B
FIG. 23C

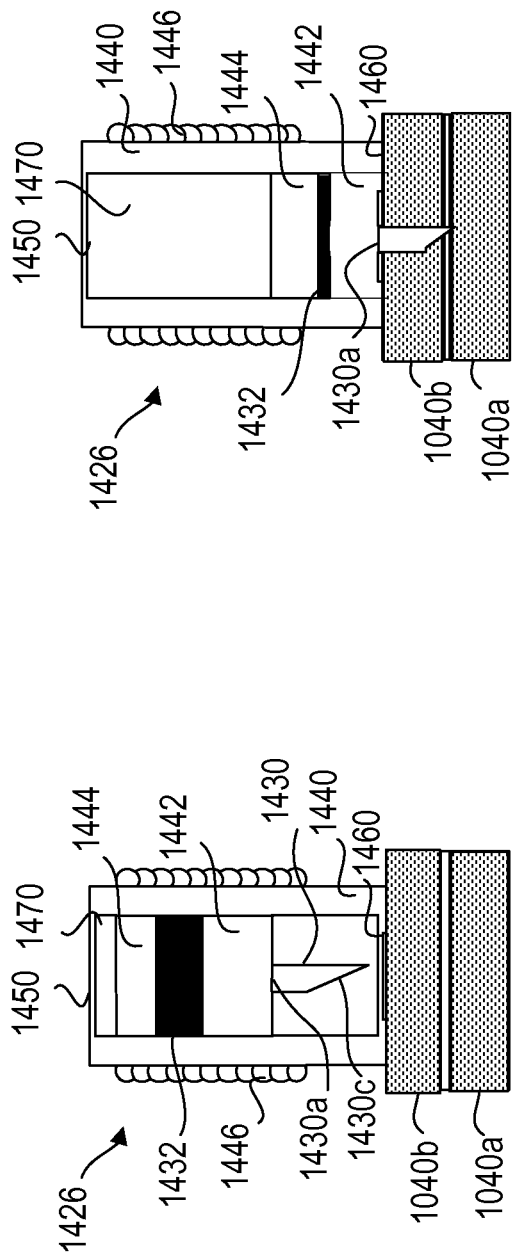

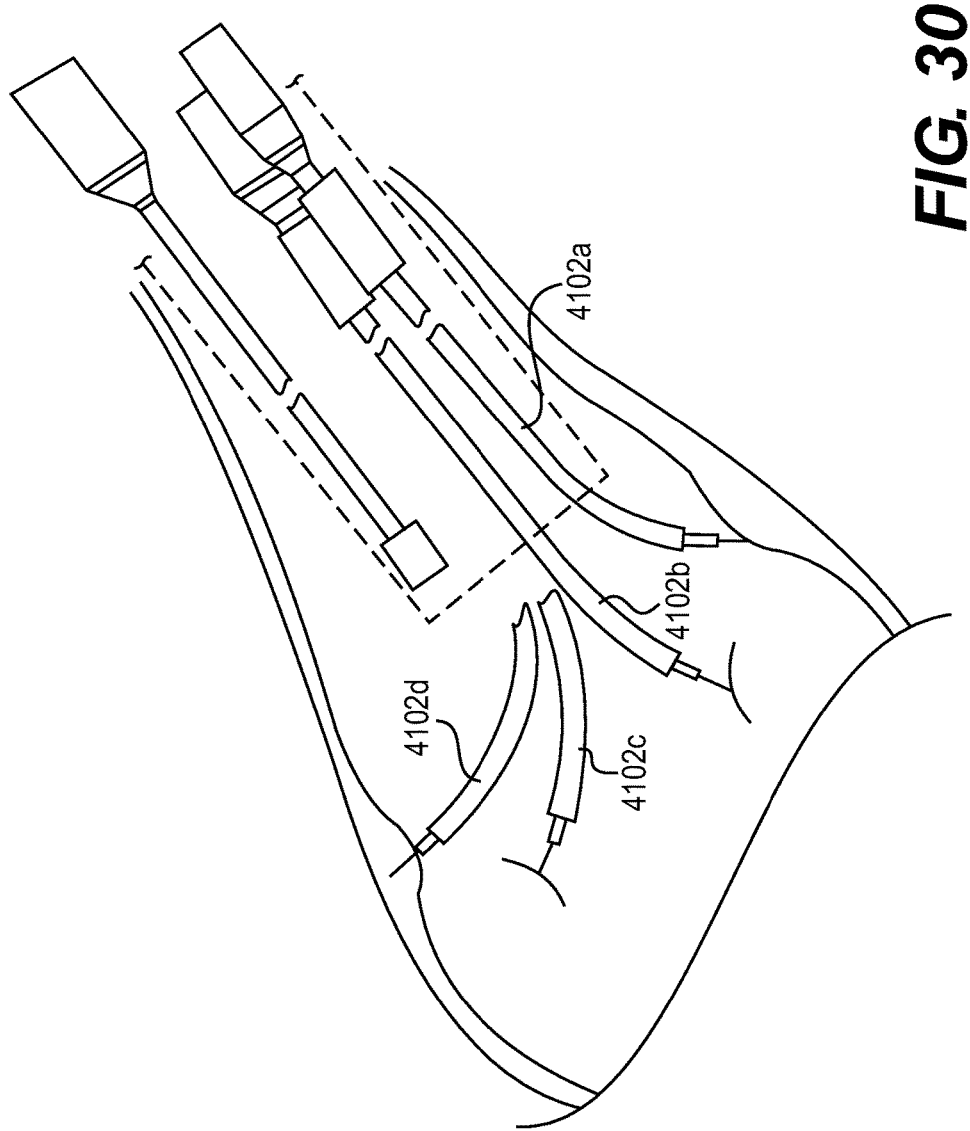

DELIVERY DEVICES AND RELATED METHODS OF USE

CROSS-REFERENCE TO RELATED APPLICATIONS

This application claims the benefit of priority from U.S. Provisional Application No. 61/798,618, filed Mar. 15, 2013, U.S. Provisional Application No. 61/799,260, filed Mar. 15, 2013, and U.S. Provisional Application No. 61/829,348, filed May 31, 2013, the entireties of which are incorporated by reference herein.

DESCRIPTION OF THE DISCLOSURE

Field of the Disclosure

This disclosure relates generally to devices and methods for delivery of substances into the body of a subject. In addition, this disclosure relates to using injection devices and techniques to inject substances into the gastrointestinal tract of a subject.

Background

Obesity is a complex metabolic condition associated with a high number of co-morbidities. Despite extensive research, there is still an unmet clinical need for a minimally invasive and effective intervention for obesity. Drugs, devices, and bariatric surgery are part of the current therapy landscape.

The gastrointestinal tract includes multiple targets for obesity therapies. The small intestine is one anatomical target for obesity therapies. The majority of digestive function, including nutrient absorption, occurs in the small intestine. The duodenum acts like a mixing bowl that combines partially digested contents (e.g., food) with secretions from the liver and pancreas to complete the digestion process. One of the intended results of gastric bypass surgery, a type of bariatric surgery, is the complete exclusion of the duodenum and proximal jejunum from exposure to digestive material. This exclusion results in reduced absorption of the digestive material. This mechanism may result in weight loss, but may also have negative side effects, such as malnutrition, susceptibility to bone breakage due to poor calcium absorption, and other potentially harmful effects.

Another anatomical target for obesity therapies is the stomach. In the stomach, procedures similar to the ones described above, may be employed. For example, surgical procedures may be carried out to remove or isolate portions of the stomach, resulting in reduced absorption of digestive material. Such surgical procedures may also produce negative side effects.

Therefore, there exists a need for methods of treatment and medical devices capable of providing therapy to areas of the gastrointestinal tract to be able to limit food intake in a minimally-invasive manner while preserving nutrient absorption.

SUMMARY

Embodiments of the disclosure provide devices and methods for treatment of the gastrointestinal tract.

According to an aspect of the disclosure, a treatment method may include treating a wall of a portion of a gastrointestinal tract of a patient. Treating the wall may include positioning one or more injection units adjacent to the wall. Treating the wall may also include affecting at least one of movement of gastrointestinal tract contents through the gastrointestinal tract and absorption of gastrointestinal tract contents by the gastrointestinal tract, by injecting material into the wall using the one or more injection units. Injecting the material may include injecting the material between layers forming at least a portion of the wall.

According to another aspect of the disclosure, a treatment method may include treating a wall of a portion of a gastrointestinal tract of a patient. Treating the wall may include inserting one or more injection units of a medical device through an anatomical passage forming at least a portion of the gastrointestinal tract. Treating the wall may also include positioning the one or more injection units adjacent to the wall. Treating the wall may also include controlling at least one of movement of gastrointestinal tract contents through the gastrointestinal tract and absorption of gastrointestinal tract contents by the gastrointestinal tract, by injecting material into the wall using the one or more injection units. Injecting the material may include injecting the material between layers forming at least a portion of the wall.

According to another aspect of the disclosure, a treatment method may include treating an organ of a gastrointestinal tract of a patient. Treating the organ of the gastrointestinal tract of the patient may include positioning one or more injection units within the organ. Treating the organ may also include restricting at least one of movement of gastrointestinal tract contents through the gastrointestinal tract and absorption of gastrointestinal tract contents by the gastrointestinal tract, by injecting material into a wall of the organ using the one or more injection units. Injecting the material may include injecting the material between layers forming at least a portion of the wall.

Additional objects and advantages of the claimed disclosure will be set forth in part in the description which follows, and in part will be apparent from the description, or may be learned by practice of the disclosure.

It is to be understood that both the foregoing general description and the following detailed description are exemplary and explanatory only and are not restrictive of the disclosure, or claims.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 1 illustrates a system for treatment of a portion of the gastrointestinal tract, having a medical device, according to an embodiment of the disclosure;

FIG. 2 is a cross-section of the medical device along line 2-2 of FIG. 1;

FIG. 7A illustrates a medical device being inserted into a portion of the gastrointestinal tract through an outer sheath, according to an embodiment of the disclosure;

FIG. 7B illustrates an end effector assembly of the medical device being positioned in a portion of the gastrointestinal tract, and a first expandable member of the end effector assembly being in a partially collapsed configuration, according to an embodiment of the disclosure;

FIG. 7C illustrates the first expandable member of the end effector assembly being in an expanded configuration, according to an embodiment of the disclosure;

FIGS. 10A-10C are schematic views of alternate embodiments of medical device configurations, according to embodiments of the disclosure;

FIGS. 13A-13C show cross-sectional side views of alternative embodiments of medical device configurations, according to embodiments of the disclosure;

FIG. 13D shows a perspective view of material for constructing a medical device, according to an embodiment of the disclosure;

FIG. 16 is a side view of an end effector assembly of the medical device of FIG. 14, according to an embodiment of the disclosure;

FIG. 17 is an enlarged view of a portion of a leg of the end effector assembly of FIG. 16, according to an embodiment of the disclosure;

FIG. 18 is an end view of a catheter of an injection unit fixed in an exit aperture on the leg shown in FIG. 17, according to an embodiment of the disclosure;

FIG. 19A is a partial side view of the injection unit of FIG. 16, with an injector in a retracted configuration, according to an embodiment of the disclosure;

FIG. 19B is a partial side view of the injection unit of FIG. 16, with the injector in a first position in the deployed configuration, according to an embodiment of the disclosure;

FIG. 19C is a partial side view of the injection unit of FIG. 16, with the injector in a second position in the deployed configuration, according to an embodiment of the disclosure;

FIG. 20A illustrates an end effector assembly of the medical device being positioned in a portion of the gastrointestinal tract, according to an embodiment of the disclosure;

FIG. 20B illustrates the end effector assembly in an expanded configuration, according to an embodiment of the disclosure;

FIGS. 22A-22E illustrate alternative configurations of the end effector assembly of the medical device of FIG. 14, according to embodiments of the disclosure;

FIG. 23A is a partial side view of a catheter of an injection unit, in accordance with an embodiment of the disclosure;

FIG. 23B is a perspective view of a distal facing surface of the catheter of FIG. 23A, according to an embodiment of the disclosure;

FIG. 23C is a partial side view of the catheter of FIG. 23A and an injector disposed in the catheter, according to an embodiment of the disclosure;

FIG. 25A is a schematic view of an injection unit with an injector in a retracted position, in accordance with an embodiment of the disclosure;

FIG. 25B is a schematic view of the injection unit of FIG. 25A, with the injector in a deployed position, according to an embodiment of the disclosure;

FIG. 30 is a schematic view of an exemplary method for treating a portion of the gastrointestinal tract, according to an embodiment of the disclosure.

DESCRIPTION

Figure 3B:
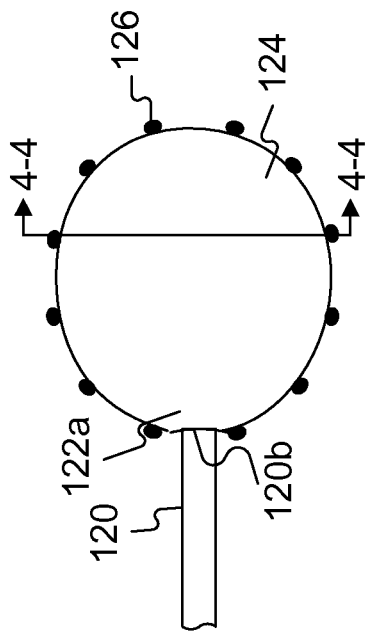
FIG. 3B is a side view of the end effector assembly of FIG. 3A, with the first expandable member in the expanded configuration, according to an embodiment of the disclosure.

Reference is now made in detail to embodiments of the present disclosure, examples of which are illustrated in the accompanying drawings. Wherever possible, the same reference numbers will be used throughout the drawings to refer to the same or like parts.

Overview

The gastrointestinal tract includes a number of organs, including, for example, the stomach and the small intestine. The stomach and the small intestine each include walls made up of a plurality of layers. Three primary layer regions include the mucosa, submucosa, and muscularis. Within the primary layer regions, there may be sublayers. For example, the submucosa layer of the small intestine may include a submucosal plexus sublayer, and the muscularis layer may include a sublayer of smooth muscle and a myenteric plexus sublayer. Embodiments of the present disclosure relate to devices and methods for treating one or more gastrointestinal tract organs, such as the stomach and small intestine, by injecting material between and/or into layers and sublayers forming walls of the one or more organs. The material may be injected in multiple different locations in the one or more organs substantially simultaneously using a multiple site injection device, or by performing a series of injections one after the other using a single site injection device.

With embodiments of the present disclosure, the injected material may create a semi-permanent barrier between the layers. Injection of the material may help control at least one of movement of gastrointestinal tract contents through the gastrointestinal tract, and/or absorption of one or more nutrients in the gastrointestinal tract contents by the gastrointestinal tract.

For example, when food enters the stomach, gastric juice in the stomach may cause digestion of proteins. At the same time protein digestion is occurring, mechanical mixing may occur by peristalsis, which are waves of muscular contractions that move along a muscle layer of the stomach wall. This may allow the mass of food to further mix with digestive enzymes. Additionally, the mucosa of the intestinal wall/membrane is coated with finger-like projections called villi, which are covered with a brush layer of microvilli. The villi and microvilli increase the surface area of the intestinal wall/membrane to aid digestion by, for example, aiding nutrient absorption. The myenteric and submucosal plexus may control movement of the intestines. The myenteric plexus may receive signals from the vagus nerve and may activate smooth muscle contraction, which may result in peristalsis. For example, smooth muscle cells and muscularis mucosae of the intestine may contract in a coordinated fashion to facilitate the movements of the villi and microvilli, exposing the surface area of the intestinal wall/membrane to digestive contents.

Injecting material between and/or into layers and sublayers forming walls of the stomach, intestines, and/or other portions of the gastrointestinal tract, may inhibit coordinated movements of those portions of the gastrointestinal tract. For example, the injected material may inhibit movements of the small intestine that facilitate microvilli exposure to digestive contents and nutrient absorption in the duodenum or other regions of the small intestine. Additionally or alternatively, the injected material may inhibit stomach and/or intestinal motility, which controls the transport and absorption of ingested calories and nutrients, and affects satiety and gastric emptying.

The following description focuses on techniques for treating obesity, but those in the art will understand that the same techniques may be employed in treating other organs without departing from the scope of the present disclosure. Moreover, a variety of injecting devices, including electrical, mechanical, or pneumatic injectors, may be employed in the disclosed methods, operating under manual or automated computer control.

Exemplary Embodiments

FIG. 1 illustrates an exemplary system 105 according to an embodiment of the present disclosure. System 105 includes a medical device 110, at least one fluid source 112 connected to medical device 110 by way of at least one fluid conduit 114, and an outer sheath 116 surrounding at least a portion of medical device 110. For purposes of this disclosure, outer sheath 116 may be constructed from an insulating polymer material such as polyamide, polyurethane, or any other suitable material.

Medical device 110 includes an elongate member 120, a handle portion 118, and an end effector assembly 122. Elongate member 120 has a proximal end 120a and a distal end 120b. For purposes of this disclosure, "proximal" refers to the end closer to the device operator during use, and "distal" refers to the end further from the device operator during use. Handle portion 118 is disposed at proximal end 120a of elongate member 120 and end effector assembly 122 is disposed at distal end 120b of elongate member 120. End effector assembly 122 includes one or more injection units 126 for delivering material to tissue layers of a portion of the gastrointestinal tract, such as in tissue layers forming the small intestine and the stomach.

FIG. 2 is a cross-section of elongate member 120 along lines 2-2 in FIG. 1. Elongate member 120 is a solid rod or tube, made from any suitable biocompatible material known to one of ordinary skill in the art having sufficient flexibility to traverse an anatomical lumen, such as lumens in the gastrointestinal tract, including an esophagus, stomach, and/or small intestine. Such materials may include, but are not limited to, rubber, silicon, synthetic plastics, stainless steel, metal-polymer composites, and metal alloys of nickel, titanium, copper cobalt, vanadium, chromium, and iron. In one embodiment, the material forming elongate member 120 may be a superelastic material such as nitinol, which is a nickel-titanium alloy. Elongate member 120 may have any cross-sectional shape and/or configuration and may be any desired dimension that can be received in one or more lumens of the gastrointestinal tract. Elongate member 120 includes at least one lumen 128 extending from proximal end 120a of the elongate member 120 to distal end 120b of the elongate member 120 for passage of fluid and/or tools to end effector assembly 122.

Figure 3A:
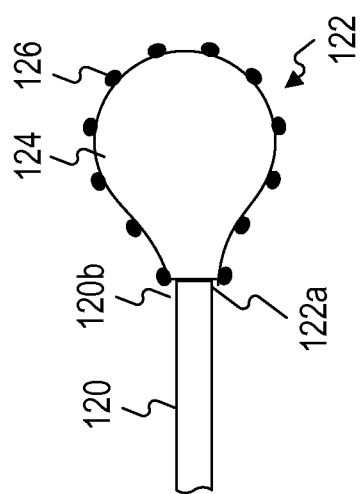
FIG. 3A is a side view of an end effector assembly of the medical device of FIG. 1, the end effector assembly including a first expandable member in a partially collapsed configuration, according to an embodiment of the disclosure.

Referring to FIGS. 3A and 3B, end effector assembly 122 includes a first expandable member 124. The phrase "expandable member" generally relates to any expandable structure, such as a balloon or other inflatable structure, regardless of the elasticity of the material comprising the structure. For example, the phrase "expandable member" may denote a thin-walled structure made of material of low elasticity (which does not stretch significantly during inflation) or highly elastic material (which does stretch significantly during inflation). For example, first expandable member 124 may be made from polyethylene terephthalate (PET), polyurethanes, polyethylenes and ionomers, copolyesters, rubbers, polyamides, silicone, latex, or any other suitable materials known in the art.

First expandable member 124 may be made integral with elongate member 120 through connection of a proximal end 122a of the end effector assembly 122 to a region of elongate member 120, such as distal end 120b of elongate member 120. The connection at proximal end 122a of end effector assembly 122 may be accomplished through any suitable means of fixedly connecting end effector assembly 122 to elongate member 120. For example, possible connections may include, but are not limited to, welding, soldering, and/or crimping.

First expandable member 124 may be in fluid communication with lumen 128 of elongate member 120. Lumen 128 may provide a fluid pathway through which a fluid, such as a liquid or gas, may pass to expand (inflate) and contract or collapse (deflate) first expandable member 124. The inflation fluid may be air, water, carbon dioxide, saline solution, or a contrast agent. In alternative embodiments, first expandable member 124 may be mechanically, electrically, or pneumatically expanded and collapsed without departing from the scope of the disclosure.

FIG. 3A shows first expandable member 124 in a partially collapsed configuration, and FIG. 3B shows first expandable member 124 in an expanded configuration. The particular expanded exterior configuration of first expandable member 124, such as the volume, width, radius, length, or other dimension, may be selected so that first expandable member 124 substantially fills the interior of an organ of the gastrointestinal tract, such as the small intestine or the stomach, in the expanded configuration, to position the one or more injection units 126 adjacent a wall of the organ. For example, in the embodiment shown in FIG. 3B, first expandable member 124 in its expanded configuration may be substantially round in shape. It is understood that the outer profile of first expandable member 124 may have an oval, elliptical, square, rectangular, cylindrical, toroidal, anatomical, or any other shape, to fit the organ being treated. Exemplary shapes are shown in FIGS. 13A-13C. For example, FIG. 13A shows elliptical or oval-shaped inflatable members 324 and 336, with injection units 326; FIG. 13B shows rectangular or cylindrical inflatable members 424 and 436, with injection units 426; and FIG. 13C shows toroidal inflatable members 824 and 836, with central openings 825 and 837 extending longitudinally therethrough, and with injection units 826.

Figure 4:
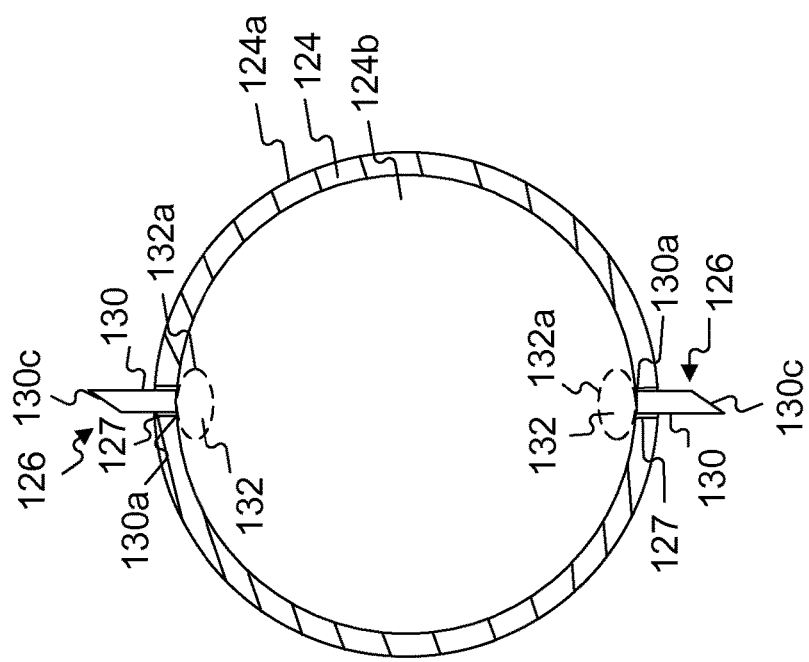
FIG. 4 is a cross-section of the end effector assembly along line 4-4 of FIG. 3B, according to an embodiment of the disclosure.

The one or more injection units 126 may be uniformly distributed on first expandable member 124 in the partially collapsed configuration and the expanded configuration. First expandable member 124 may act as a positioning mechanism to position the one or more injection units 126 adjacent the organ wall. Although the depicted embodiment includes twelve injection units 126, end effector assembly 122 may include a greater or lesser number of injection units 126. Referring to FIG. 4, each individual injection unit 126 may be fixed in an exit aperture 127 on first expandable member 124 and extend outwardly of an exterior surface 124a of first expandable member 124.

Each individual injection unit 126 includes an injector 130. Injector 130 may be a conventional needle, including, for example, a micro-needle, having a proximal end 130a, a sharpened distal point 130c, and a hollow interior. Injector 130 may be provided within exit aperture 127 with proximal end 130a of injector 130 positioned within an interior space 124b of first expandable member 124, and distal point 130c extending outwardly of exterior surface 124a of first expandable member 124. The portion of injector 130 within exit aperture 127 may be fixed to exit aperture 127 by welding, soldering, and/or crimping. First expandable member 124 may be a positioning mechanism configured to position each individual injector unit 126 adjacent the organ wall as first expandable member 124 expands from the partially collapsed configuration to the expanded configuration.

Injector 130 may have any size, shape, and/or configuration. In the exemplary embodiment, injector 130 may have a generally cylindrical shape. The particular dimensions of injector 130, such as the length and/or diameter, may be selected to penetrate tissue and deliver materials at a predetermined depth. In particular, injector 130 may be dimensioned to enter a wall of an organ as deep as the layer of smooth muscle, without penetrating the myenteric plexus. It is contemplated that injector 130 may have any other shape and/or configuration that may accommodate the desired depth. It is also contemplated that the injector 130 may be dimensioned to penetrate to a shallower depth or deeper depth, depending on the type of treatment being performed.

A dispenser 132 may be a part of injector 130 and may be positioned adjacent proximal end 130a of injector 130 within interior space 124b of first expandable member 124. Dispenser 132 may be a fluid container configured to retain material for injection between and/or into one or more tissue layers of a gastrointestinal tract organ.

In the exemplary embodiment, dispenser 132 may be a fluid bulb having an impermeable membrane. In other embodiments, dispenser 132 may be an elastomeric container. In alternative embodiments, dispenser 132 may have a housing, and at least a portion of the housing may have a collapsible wall. In each of these embodiments, dispenser 132 may be positioned adjacent proximal end 130a of injector 130 so that, as the dispenser collapses and/or ruptures, the material may be delivered into an opening at proximal end 130a of injector 130 for delivery to tissue via an opening at distal point 130c.

Figure 5B:
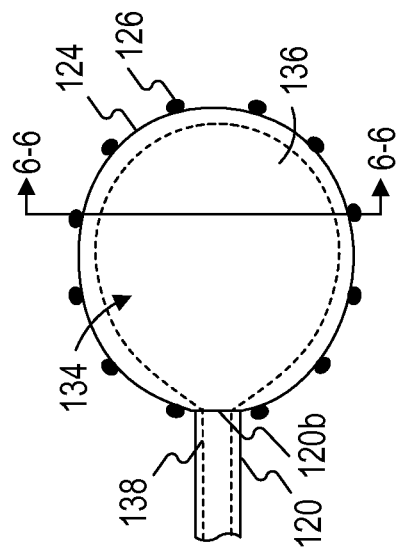
FIG. 5B is a side view of the end effector assembly of FIG. 5A with the second expandable member in the expanded configuration, according to an embodiment of the disclosure.
Figure 5A:
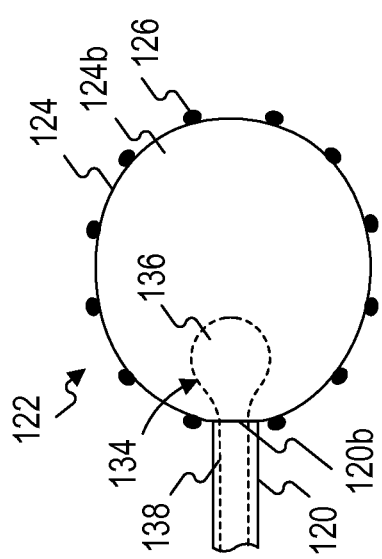
FIG. 5A is a side view of the end effector assembly of FIG. 3B, the end effector assembly including a second expandable member in a collapsed configuration, according to an embodiment of the disclosure.

Referring now to FIGS. 5A-5B, an injection mechanism 134 may be positioned within first expandable member 124 adjacent to distal end 120b of elongate member 120. The phrase "injection mechanism" generally relates to any known structure or mechanism configured to exert a force on dispenser 132 or a like fluid reservoir so as to deliver the material from dispenser 132 into injector 130 for delivery into the tissue. In this embodiment, injection mechanism 134 includes a second expandable member 136. Second expandable member 136 is connected to a tube 138 which extends proximally through lumen 128 of elongate member 120. In some embodiments, tube 138 may be operably connected to an actuator (not shown) on handle portion 118 and may be movable relative to elongate member 120 in order to advance second expandable member 136 from a retracted position within lumen 128 of elongate member 120 to a deployed position distally of distal end 120b of elongate member 120. In other embodiments, injection mechanism 134 may be inserted into lumen 128 of elongate member 120 via a port 119 (FIG. 1) on handle portion 118, and may be manually deployed and/or retracted.

Tube 138 includes a lumen 139 in fluid communication with the same and/or different fluid source 112. Lumen 139 provides a fluid pathway for a fluid, such as a liquid or gas, to pass to expand (inflate) and contract or collapse (deflate) second expandable member 136. FIG. 5A shows second expandable member 136 in a partially collapsed configuration, and FIG. 5B shows second expandable member 136 in an expanded configuration. The particular expanded exterior configuration of second expandable member 136, such as the shape, volume, width, radius, length, or other dimension, may be selected so that second expandable member 136 substantially fills the volume within interior space 124b of first expandable member 124.

Figure 6:
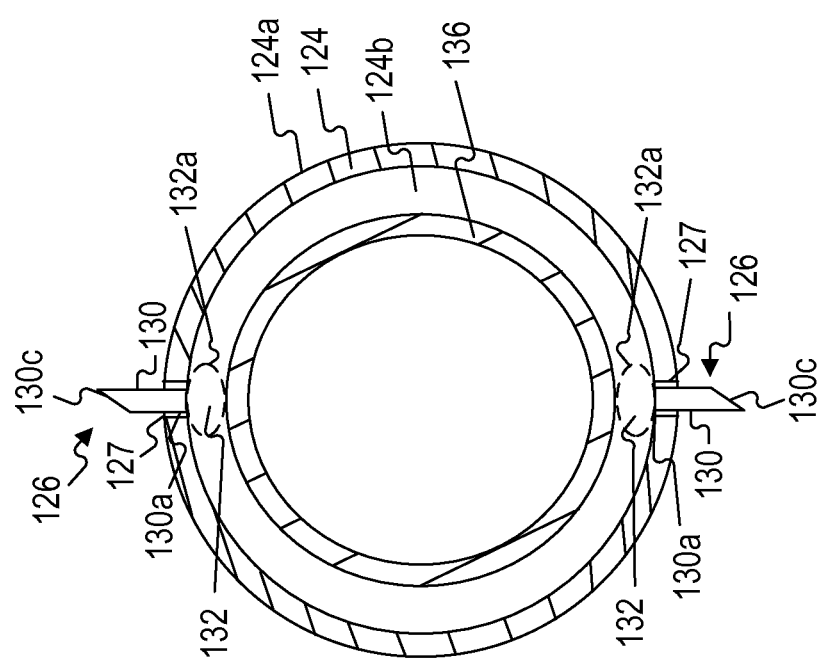
FIG. 6 is a cross-section of the end-effector assembly along line 6-6 of FIG. 5B, according to an embodiment of the disclosure.

FIG. 6 is a cross-section of end effector assembly 122 along lines 6-6 in FIG. 5B. As shown in FIG. 6, when second expandable member 136 is expanded to the expanded configuration, second expandable member 136 may exert a force on dispenser 132. Upon further expansion of second expandable member 136, pressure may rise on dispenser 132 and rupture impermeable membrane 132a. The material may then be introduced into injector 130 for delivery through distal point 130c.

Figures 7D, 7E:
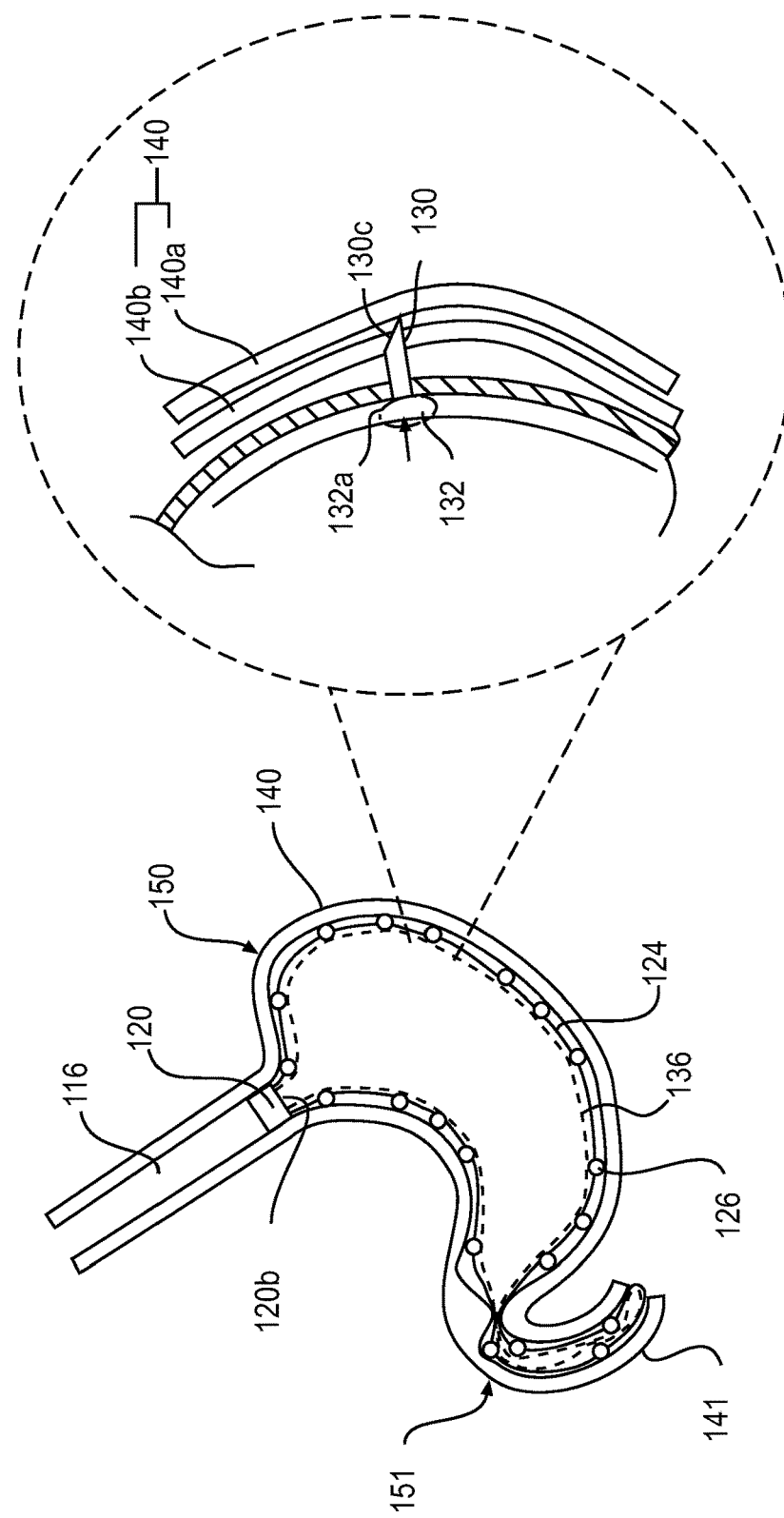
FIG. 7D illustrates a second expandable member of the end effector assembly being inflated in the first expandable member, according to an embodiment of the disclosure.
FIG. 7E illustrates an injection of material between two tissue layers of a wall in a portion of the gastrointestinal tract, according to an embodiment of the disclosure.

FIGS. 7A-7E illustrate a method for treating one or more gastrointestinal tract organs in accordance with an embodiment of the present disclosure. In particular, FIGS. 7A-7C illustrate a method for treating a stomach 150 and a portion of a small intestine 151, such as the duodenum, or another portion downstream of the duodenum. It should be understood that although the method shows treatment of the stomach 150 and small intestine 151 simultaneously, it is contemplated that only one of the two organs may be treated, or both organs may be treated one after the other.

Referring to FIGS. 7A and 7B, medical device 110 (see FIG. 1) is inserted into the esophagus of a patient, and may be advanced to the stomach 150 through an outer sheath 116 (FIG. 7A). Once a distal end of the outer sheath 116 is positioned at the entrance to the stomach 150 (or in the stomach 150), the end effector assembly 122 may be advanced distally out of outer sheath 116 (FIG. 7B). This may be achieved by, for example, pushing elongate member 120 distally relative to outer sheath 116, or pulling outer sheath 116 proximally relative to elongate member 120. Any suitable actuator on handle portion 118 may be used to effect deployment of end effector assembly 122.

Once end effector assembly 122 has been removed from outer sheath 116, inflation fluid is delivered through lumen 128 to first expandable member 124 to inflate first expandable member 124 from a partially collapsed configuration (FIG. 7B) to an expanded configuration (FIG. 7C). When fully expanded, expandable member 124 may have an anatomical shape similar to the inside of the stomach 150 and small intestine 151, positioning each injection unit 126 adjacent an interior surface of each of the organs (FIG. 7C). It should be understood that the expandable member may also have alternative shapes. It should also be understood that, when inflated, the first expandable member 124 may take the shape of the inside of the stomach 150 without entering the small intestine 151. Alternatively, the outer sheath 116 and end effector assembly 122 may be positioned at the entrance to the small intestine 151, such that when the first expandable member 124 is inflated, it may take the shape of the small intestine 151. It is also contemplated that other portions of the small intestine 151, in addition to or in place of the duodenum, may be treated using the end effector assembly 122 by positioning the end effector assembly 122 further within the small intestine 151.

Further expansion of first expandable member 124 causes the injector 130 of each injection unit 126 to pierce one of the walls 140 and 141. The penetration depth may be monitored and controlled in a number of ways. For example, injector 130 may be dimensioned to penetrate one of the walls 140 and 141 and deliver material at predetermined depth (i.e., injector 130 may be a single predetermined length). Additionally and/or alternatively, injector 130 may be provided with radiopaque markers that can be visualized as injector 130 is penetrating tissue. In further embodiments, the device may include an actuator that may enable operator to simultaneously advance injectors 130 in known increments. Alternatively, the injector 130 may include a flange, stop, or shoulder to press up against tissue to control the depth of penetration of the injector 130.

The procedure continues with the physician advancing injection mechanism 134 within lumen 128 of elongate member 120. In particular, the physician may move tube 138 of injection mechanism 134 relative to elongate member 120 in order to advance second expandable member 136 from a retracted position within lumen 128 of elongate member 120 to a deployed position within interior space 124b of first expandable member 124. The mechanisms for extending second expandable member 136 into interior space 124b of first expandable member 124 are well known in the art and need not be discussed here.

Once second expandable member 136 is in the deployed position, inflation fluid may be delivered through lumen 139 of tube 138 to inflate second expandable member 136 from a collapsed configuration to an expanded configuration (FIGS. 7D and 7E). As second expandable member 136 expands, second expandable member 136 may come into contact with the one or more dispensers 132 associated with the one or more injection units 126. Further expansion of second expandable member 136 may exert a force on dispensers 132. Upon application of sufficient force, the impermeable membrane 132a of each dispenser 132 may rupture injecting material from dispensers 132 into injectors 130 for delivery between and/or into tissue layers of the stomach 150 and/or small intestine 151. It is understood that dispensers 132 may take any number of shapes other than that disclosed in the figures, such as, for example, a bellows shape.

The injected material or compound may be a liquid (e.g., saline), a gel, or a liquid/gel that cures into a solid or fluid. For example, the material may include a hydrogel (e.g., PEG, hyaluronic acid, polyacrylamide gel, chitosan, sodium alginate, PLA, or hydrogel mixture) which, after injection, may be cured by cross-linking as is known in the art. Additionally or alternatively, the material may be saline or a similar inert compound, or in the form of a fluid, gas, gel, or composite fluid. It is also contemplated that the material could be biostable, biodegradable, or bioabsorbable. For example, fatty acid esters with low molecular weight can be prepared to have variable absorption rates and could be injected with no solvent carrier. Alternatively, aqueous based materials could be injected in a manner that allows water to diffuse out, leaving a barrier material behind to be slowly absorbed or to be relatively permanent. Examples of degradable materials include carboxymethyl cellulose, copolymers of esters such as PLA, PGA, PLGA, PCL, with solubilizing blocks such as PEG or PVA. Absorbable materials include gels, some of which solidify at body temperature and are only slowly reabsorbed. Surgical glues may also be used. Permanent materials may include polyacrylic acid, polyHEMA, PVA, and the like. It is also contemplated that a dye could be incorporated that would enable the physician to tell if the injection was successful.

The injected material may have any desired composition, viscosity, and/or biodegradability characteristics so as to permit the injected material, such as a cured hydrogel, to carry and deliver a drug over an extended period of time, such as, for example, several months or years. Further, the injected material, such as a hydrogel, may include high expansion properties (e.g. expanding between approximately five to approximately ten times its original volumetric size). As such, a large physical barrier may be achieved while using a small volume/amount of the injected material. Additionally, such a hydrogel may be absorbable into walls 140 and 141.

The material may be injected into a space between two tissue layers 140a, 140b in wall 140 (or similar layers (not shown) in wall 141) to separate, and maintain separation between the two layers. For example, the material may be injected between the myenteric plexus and a layer of smooth muscle in the small intestine 151. The injected material may create a semi-permanent barrier between the layers. Injection of the material may inhibit coordinated movements that facilitate microvilli exposure to digestive contents and nutrient absorption in the small intestine 151, and/or may inhibit stomach and/or intestinal motility, which controls (e.g., reduces) the transport and absorption of ingested calories and nutrients, and affects satiety and gastric emptying.

The injections may be performed at sites spaced equidistantly from one another along wall 140 and/or wall 141, so as to uniformly treat one or both of the organs. It is contemplated, however, that first expandable member 124 may be partially expanded, and end effector assembly 122 may be positioned adjacent a predetermined site in the stomach 150 and/or small intestine 151, to selectively treat that site.

Figure 8A:
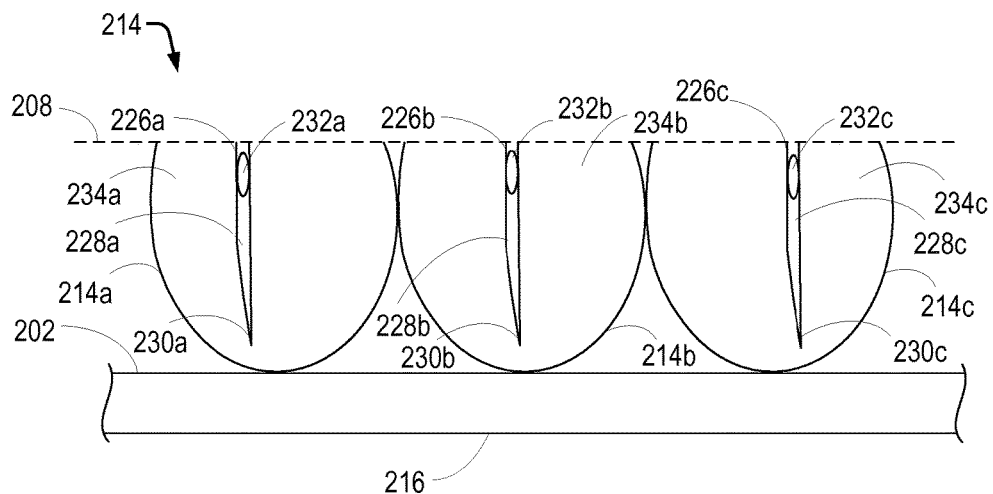
FIG. 8A is a schematic view of an array of delivery units, according to an embodiment of the disclosure.

FIG. 8A is a schematic view of an array of delivery units 214. The delivery units 126 may include the features of the delivery units 214. The delivery units 214a, 214b, and 214c may rest along the inner surface of an outer balloon 202, which in turn is placed along the inner surface of an organ wall 216, such as the wall 140 of the stomach 150, or the wall 141 of the small intestine 151. The first expandable member 124 may include the features of the balloon 202. In the example shown here, the delivery units 214 may be capsule-shaped, having a rounded cross-section. Those skilled in the art will appreciate that any suitable cross-section such as circular, rectangular, oval, irregular, or the like may also be contemplated. Although, only three delivery units are shown, it may be contemplated that any suitable number of delivery units 214 may be employed, and in any suitable arrangement to position the delivery units 214 in targeted areas. For example, the deliver units 214 can be arranged in multiple circumferential arrays, targeted arrays for a particular location within an organ, and/or arrays tailored to the shape of the organ the balloon 202, and a balloon 208, are being introduced into. The injection mechanism 134 may include the features of the balloon 208.

Each delivery unit 214a, 214b, and 214c may include a piercing member such as a needle 226a, 226b, and 226c, respectively. The needles 226a, 226b, and 226c may be elongated with a sharp needle tip 230a, 230b, and 230c, which are capable of piercing a tissue surface such as the organ wall 216. Those skilled in the art will appreciate that any suitable piercing member may be contemplated without departing from the spirit and scope of the present disclosure. Suitable examples may include, but are not limited to, blades, cutters, or the like.

In the example shown here, the needles 226a, 226b and 226c are hollow each defining a needle lumen 228a, 228b, and 228c, respectively. In addition, each needle 226a, 226b and 226c may include an aperture 232a, 232b, and 232c disposed along a portion of length of the needles. Each aperture 232a, 232b, and 232c may provide a fluid connection between the needle lumen 228a, 228b, and 228c and a respective reservoir 234a, 234b, and 234c. Further, an external force such as pressure may be applied on the reservoirs 234a, 234b, and 234c, which may deliver the material (not shown) contained within the reservoirs to the needle lumens 228a, 228b, and 228c via respective needle apertures 232a, 232b, and 232c. Further application of pressure on the reservoirs 234a, 234b, and 234c may allow delivery of the material (not shown) held within the needle lumens 228a, 228b, and 228c to the target tissue.

It is contemplated that the needles 226a, 226b, and 226c may be open at the needle tip 230a, 230b, and 230c and include the apertures 232a, 232b, and 232c enabling delivery of the material (not shown) at a certain depth in the organ wall 216. In such instances, the material (not shown) may be delivered to the tissue only when the aperture is in fluid communication with the reservoir. Alternative configurations of the needles 226 may include, but are not limited to, slotted needles, or the like.

Needles 226 may be made of any suitable biocompatible material having enough stiffness to pierce a tissue. Suitable examples may include, but are not limited to, metals, polymer, composite, or the like. In certain instances, alloys such as Nitinol™ may also be contemplated. Those skilled in the art will appreciate that any suitable material allowing the desired function may be employed without departing from the scope and spirit of the present disclosure. For example, the needles 226 may be made from a material that allows for folding or bending to assist with insertion of the device. It is also understood that the needles 226 can be oriented at any non-normal angle with respect to the tissue that will provide for pierce the tissue. For example, needles may be oriented at a 45 degree angle with respect to the tissue.

Figure 8B:
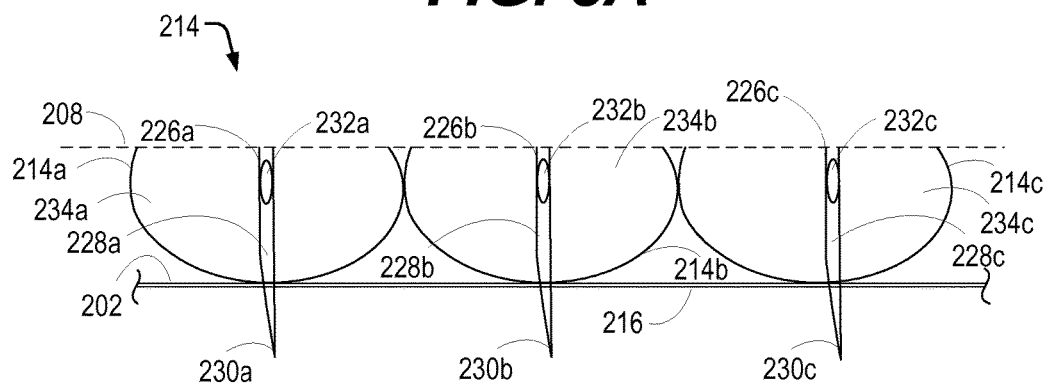
FIG. 8B is a schematic view of the delivery units of FIG. 8A with the needles piercing a wall of a portion of the gastrointestinal tract, according to an embodiment of the disclosure.

FIG. 8B is a schematic view of the exemplary delivery units 214 of FIG. 3A with the needles 226a, 226b, and 226c piercing the organ wall 216. As previously discussed, the outer balloon 202 may be fully inflated to come in contact with the organ wall 216 (see FIG. 3A), and further inflation of the outer balloon 202 may allow the needles 226a, 226b, ad 226c to pierce the organ wall 216.

In the illustrated embodiment, the delivery units 214 are in partially compressed state such that the needle tips 230a, 230b, and 230c pierce the organ wall 216. Once, the needles 216a, 216b, ad 216c reaches a pre-determined depth within the tissue, the inner balloon 208 may be inflated to compress the reservoirs 234a, 234b, and 234c such that the material may enter the needle lumens 228a, 228b, and 228c. Further, inflation of the inner balloon 208 may allow delivery of the material through the needle tip 230a, 230b, and 230c.

While not explicitly shown, inflation of the inner balloon 208 compresses the reservoirs 234a, 234b, and 234c facilitating delivery of the material into the needle lumens 228a, 228b, and 228c through the apertures 232a, 232b, and 232c. Further inflation of the inner balloon 208 may deliver the material into the organ tissue. In addition, delivery rate of the material may be controlled by controlling the inflation rate and pressure of the inner balloon 208. In addition, the formulation of the material may also affect its delivery rate into the organ wall 216. Other factors that may affect the delivery rate include the diameter of the needle lumens 228a, 228b, and 228c, the profile of the needle tips 230a, 230b, and 230c, or the like. Additional factors may also affect the material delivery rate.

It is also contemplated that the balloons 202 and 208 may be configured to inflate and/or deflate into various shapes designed by varying the material properties and wall thicknesses. Thus, the material employed to manufacture the balloons 202 and 208 may employ either single or a group of materials to achieve the desired inflation/deflation and drug flow conditions. For example, as shown in FIG. 13D, an inflatable member 900 that may represent balloon 202, balloon 208, and/or any of the above-described inflatable members, may include alternating strips or bands of two materials 902 and 904 having different characteristics (e.g., material properties). For example, the material 902 may be more elastic than the rigid 904. The elasticity of the material 902 may help the inflatable member take the contours of an organ wall. The relative rigidity of the material 904 may provide added strength for exerting a force on and actuating one or more of the injection units. In contrast, a single material with various durometers may also be used to manufacture the balloons 202 and 208.

Figure 9A:
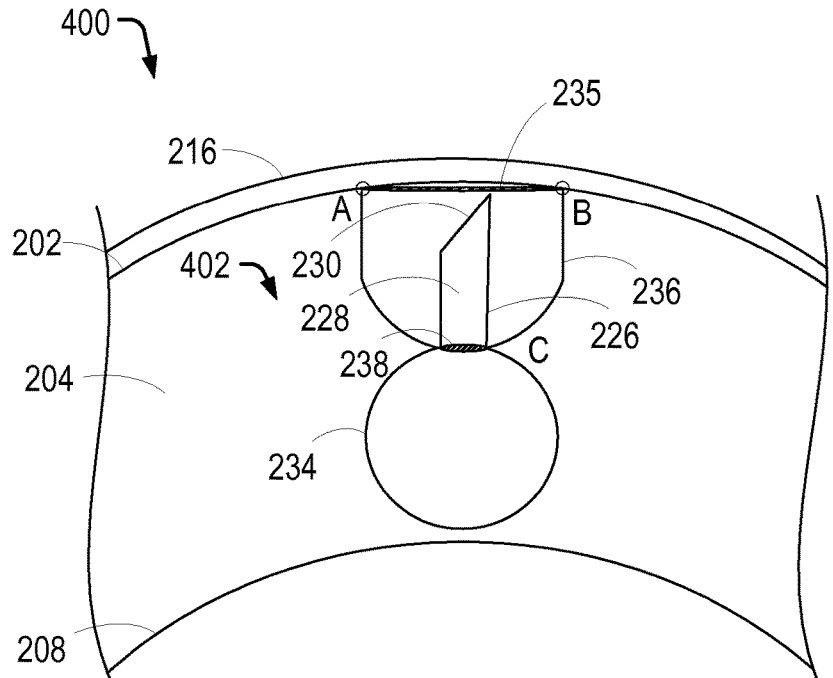
FIG. 9A is a schematic view of an exemplary medical device disposed in the gastrointestinal tract, according to an embodiment of the disclosure.

FIG. 9A is a schematic view of an exemplary medical device 400, according to embodiments of the present disclosure. It is contemplated that the end effector assembly 122 may include the features of the device 400. For example, each of the injection units 126 may include the features of a delivery unit 402 of the device 400. The delivery unit 402 may be disposed within a first internal cavity 204 of the outer balloon 202. The delivery unit 402 includes a needle 226 coupled to a reservoir 234 such that a needle lumen 228 may remain in fluid communication with the reservoir 234.

It is contemplated that the delivery unit 402 may be embedded within the first internal cavity 204 at an intersection C. The intersection C may include a membrane 238 configured to couple the needle 226 to the reservoir 234, while being disposed in between the needle 226 and the reservoir 234. Those skilled in the art will appreciate that the membrane 238 may include any suitable structures including, but not limited to, a pouch, or the like.

According to an embodiment, the membrane 238 may be configured and arranged to restrict entry of the material contained within the reservoir 234 to the needle lumen 228. Further, the membrane 238 may be made from any suitable flexible material, which may allow entry of the material into the needle lumen on application of an external pressure on the reservoir. Examples may include polymer, composite, alloys, or the like. In some embodiments, the membrane 238 may have flexibility depending on a variety of factors including: 1) sufficient strength to avoid inadvertent entry of material in the needle lumen, 2) compression force required to burst the membrane 238 to deliver the material contained within the reservoir 234 to the needle lumen 228, and so forth.

In addition, the medical device 400 may include a pocket 236 such that the needle may rest inside it. As shown, the pocket 236 may have a cup-shaped configuration having a semi-circular cross-section. It is noted that other suitable shapes and cross-sections of the pocket may also be contemplated. Further, the semi-circular pocket 236 may define an outer ring 235 that may be attached to the outer balloon at two ends A and B of the outer ring 235.

In the illustrated embodiment, the needle 226 may rest within the pocket 236 such that the needle tip 230 may remain under the outer ring 235 of the pocket 236. This configuration may avoid any inadvertent puncture of the surrounding tissue by the needle tip 230, while deploying the medical device 400 inside a body cavity. Once the device 400 is placed at a target region, e.g., adjacent the stomach 150 and/or small intestine 151, the outer balloon 202 may be inflated. Inflation of the outer balloon 202 may stretch the pocket 236 such that the outer ring 235 may be stretched along the AB line. As a result, the depth of the pocket 236 may decrease. Further inflation of the outer balloon 202 may stretch the pocket 236 to flatten it, thus forcing the needle to puncture into the organ wall 216 through outer balloon 202 (as shown in FIG. 9B).

Figure 9B:
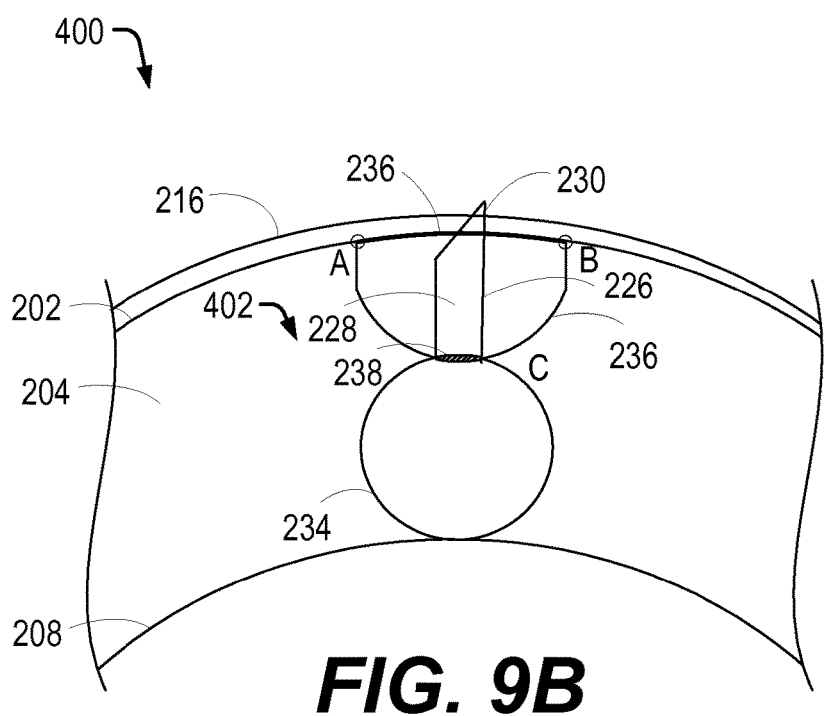
FIG. 9B is a schematic view of the medical device of FIG. 9A in one expanded configuration, where the needle of the delivery unit pierces a wall of a portion of the gastrointestinal tract, according to an embodiment of the disclosure.

Once the needle 226 is placed within the organ wall 216, the inner balloon 208 may be inflated such that it contacts the reservoir 234 as shown in FIG. 9B. Further inflation of the inner balloon 208 may compress the reservoir 234, which may rupture the membrane 238. This may allow delivery of the material contained within the reservoir 234 into the needle lumen 228, which on further inflation of the inner balloon 208 may deliver the material into the organ wall 216.

In one embodiment, hydrogel may be disposed within the membrane 238. In such instances, the compression of reservoir 234 during inflation of the inner balloon 208 may burst the membrane 238, which may deliver a combination of hydrogel and the material (contained in the reservoir 234) to the organ wall 216.

In an embodiment, the pocket 236 and the membrane 238 may be made from an easy to puncture biocompatible material, which may include a polymer, for example. Those skilled in the art will appreciate that any suitable biocompatible material may be employed to manufacture the pocket 236 and the membrane 238, without departing from the scope and the spirit of the present disclosure.

Turning now to FIGS. 10A, 10B, and 10C, schematic views of exemplary medical devices 500, 500', and 500" are depicted. It is contemplated that the injection units 126 may include the features of the medical devices 500, 500', and/or 500". The embodiment of FIG. 10A may include an array of delivery units having individual delivery units 502a and 502b disposed within the outer balloon 202. Each delivery unit 502a and 502b may include a needle 226a and 226b having its distal needle tip 230a and 230b (as shown in FIGS. 8A-8B) in communication with a pouch 242a and 242b, respectively. Each pouch 242a and 242b may further include the material 244.

It is contemplated that each pouch 242a and 242b may be made up of an easy-to-puncture material such that the needle tip may be capable of puncturing the pouches. Exemplary materials may include a biocompatible polymer, an alloy, or the like. These are just examples and are not intended to limit the scope of the disclosure.

As shown, the inner balloon 208 may be inflated to compress the delivery units 502a and 502b, which may allow the needles 226a and 226b to puncture the pouches 242a and 242b such as to deliver the material 244 to the target tissue. In contrast to the previous embodiments, inflation of the inner balloon 208 is configured to place the needles 226a and 226b within the organ wall 216 followed by delivery of material 244 into the tissue. Once the needles 226a and 226b puncture the organ wall 216 at a predetermined depth, further inflation of the inner balloon 208 delivers the material 244 contained within the pouch 242a and 242b to the tissue. In an implementation, the needle apertures 232a and 232b positioned inside the pouches 242a and 242b dictates the depth to which the needles 226a and 226b will pierce the target tissue.

FIG. 10B shows a medical device 500' according to another embodiment of the present disclosure. Here, the delivery unit 502 includes the reservoir 234 containing the material 244 and the needle 226. Unlike the embodiment shown in FIG. 10A, the delivery unit 502 includes a flexible membrane 246, which may be positioned to separate the needle 226 from the reservoir 234. Moreover, the delivery unit 502 may be disposed in the cavity of the outer balloon 202. In an implementation, the inner balloon 208 may be inflated to compress the delivery unit 502 and more particularly the needle 226 such as to puncture the membrane 246 and thus the reservoir 246. Further inflation of the inner balloon 208 may puncture the outer balloon 202 and deliver the material 244 contained within the reservoir 246 to the target tissue. The needle apertures 232 while positioned inside the reservoir 234 may allow delivery of the material 244 to the organ tissue.

In contrast, FIG. 10C shows a medical device 500" that includes both the needle 226 and the material 244 disposed within the delivery unit 502. It is contemplated that there will be no requirement for a separate reservoir in this embodiment. Further, the delivery unit 502 may include the membrane 246 structured and arranged to prevent any inadvertent puncture of the outer balloon 202 through the needle 226. Inflation of the inner balloon 208 may pierce the membrane 246 and thus the outer balloon 202, thereby delivering the material 244 to the target tissue. As inflation of the inner balloon 208 facilitates both positioning of the needle 226 and delivery of the material 244 to the target tissue, it may be contemplated that the delivery unit 500" allows continuous delivery of the material 244 to the targeted tissue, based on the rate at which the inner balloon 208 is inflated.

Although a single aperture 232 is shown in embodiments 10A-10C, it may be contemplated that the needle 226 may include two or more apertures 232 and/or perforations, which may allow delivery of a large quantity of the material 244 to the tissue.

Figure 11:
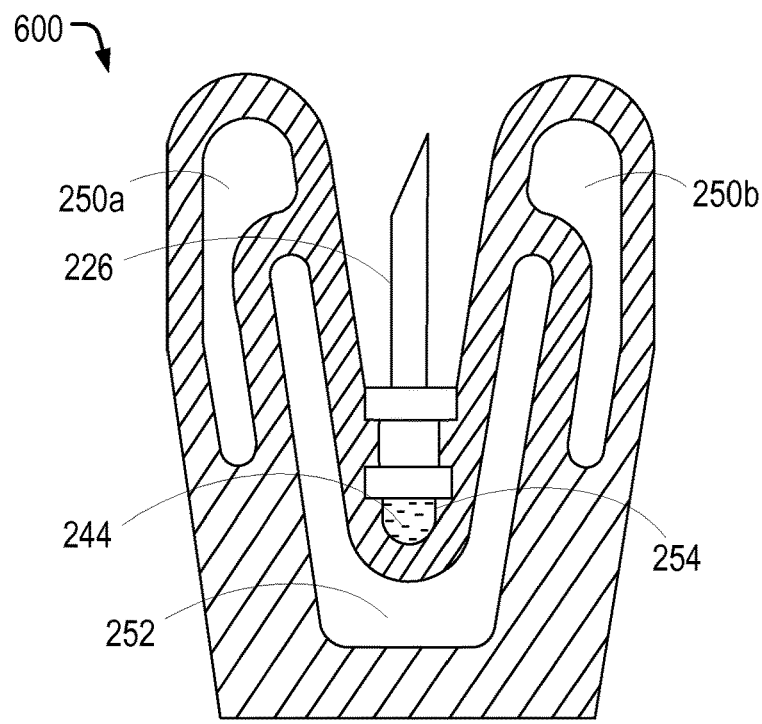
FIG. 11 is a schematic view of an exemplary delivery unit, according to an embodiment of the disclosure.
Figure 12:
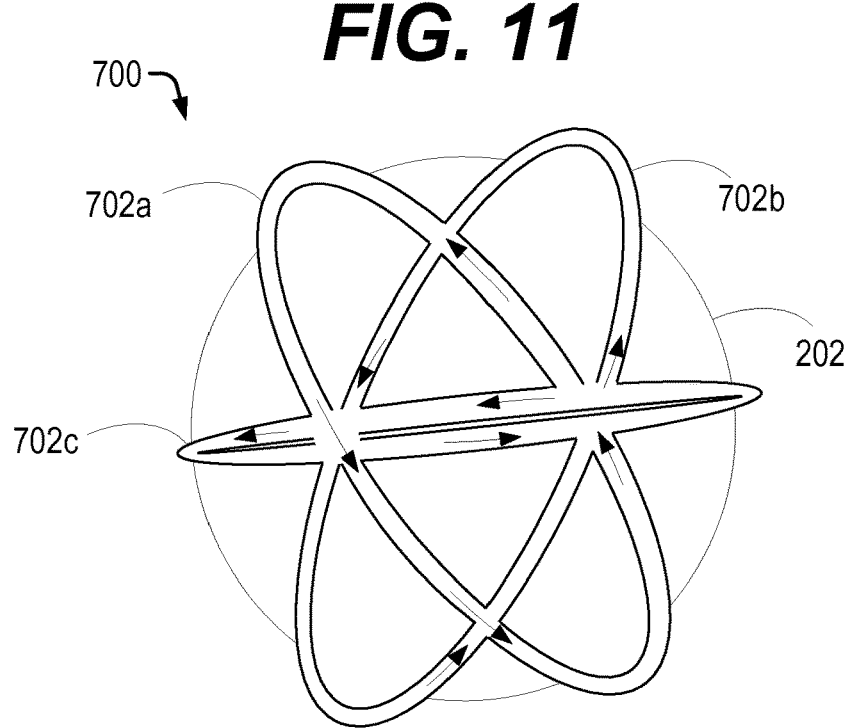
FIG. 12 is a schematic view of an exemplary medical device with multiple delivery units, according to an embodiment of the present disclosure.

A further embodiment of the medical device will be described with reference to FIGS. 11 and 12. In some embodiments, the medical device 700 (as shown in FIG. 12) includes one or more delivery units 600 each having a protective tubing network, which will be discussed in detail in conjunction with FIG. 11. According to an example, the protective tubing network may avoid any inadvertent puncture of the surrounding tissue, while the needle 226 passes through a body cavity. In addition, the protective tubing network may be configured and arranged to deliver the material through the needle, as needed.

The delivery unit 600 includes a needle 226 attached to a reservoir 254 containing the material 244. In addition, the delivery unit 600 includes a protective tubing network having lumens for changing the shape of the delivery unit 600. These lumens include needle protector lumens 250a and 250b and a needle deployment lumen 252, which may extend lengthwise through the exemplary conduit. The delivery unit 600 may each be configured to transition between a closed configuration and an open configuration. In the closed configuration (as shown in FIG. 11), the needle protector lumens 250a and 250b and the needle deployment lumen 252 are configured to protect the needle, while being disposed on either sides. However, in the open configuration, the needle protector lumens 250a and 250b and the needle deployment lumen 252 may be extended to allow the needle to come out. An inflation fluid such as a gas, saline, or the like may be employed to pressurize the needle protector lumens 250a and 250b and the needle deployment lumen 252 to transition between the open and closed configurations. Although not shown, mechanical pressure such as expansion of the inner balloon may also be employed to allow transition of delivery unit 600, and thus the lumens (250a, 250b and 252) from the closed configuration to the open configuration.

The needle protector lumens 250a and 250b may protect the needle 226 from piercing the surrounding tissue while the device is being deployed to the site. For example, the needle-protector lumens 250a and 250b may be inflated using the inflation fluid, which may extend beyond and protect the needle 226 during insertion steps.

Once the device has been deployed at the site, the needle-protector lumens 250a and 250b may be deflated and the needle deployment lumen 252 may be inflated (with air or saline or therapeutic drug), forcing the needle 226 into the tissue, thus delivering the material 244, contained in the reservoir 254, through a material delivery lumen of the needle.

As shown in FIG. 12, the medical device 700 may include one or more conduits 702a, 702b, and 702c attached to an external surface of an outer balloon 202. Each conduit 702a, 702b, and 702c may include a plurality of delivery units 600 (as shown in FIG. 11) disposed thereon. A plurality of conduits running lengthwise through the conduits 702a, 702b, and 702c may carry inflation fluid such as a gas or a liquid, and the flow of fluid in the various lumens can be manipulated to change the shape of the delivery units 600 (as shown in FIG. 11).

Although only three conduits 702a, 702b, and 702c are shown, those skilled in the art will appreciate that any number of conduits may be used based on the application. Similarly, the number of delivery units disposed within the conduits may also vary. Further, the conduits 702a, 702b, and 702c may extend around the outer balloon 202 in any suitable manner. According to an example, the configuration of conduits may vary such that the diameter of the conduits may vary along their length.

The illustrated embodiment may also allow multiple materials to be delivered through the multi-site delivery units on a continuous basis, as may be controlled by a physician. To accomplish this, one or more reservoirs 254 of one or more delivery units 600 may be filled with different materials 244. In addition, different lumens associated with the different materials 244 may be inflated and/or deflated in a suitable manner such as to deliver different materials 244 to the target tissue. Alternatively, both of the different materials 244 may be delivered to the target tissue at once.

In addition, the medical device illustrated in embodiments of the present disclosure may be manufactured using a variety of manufacturing methods. Examples may include, but are not limited to, stamping, press rolling, soldering, brazing, molding, or the like. Further, suitable materials employed to manufacture the device may include any suitable biocompatible material such as metals including, stainless steel, aluminum, titanium, polymers, composites, or the like. The manufacturing methods and materials are presented here as just examples, and hence, are not intended to limit the scope of the present disclosure.

Figure 14:
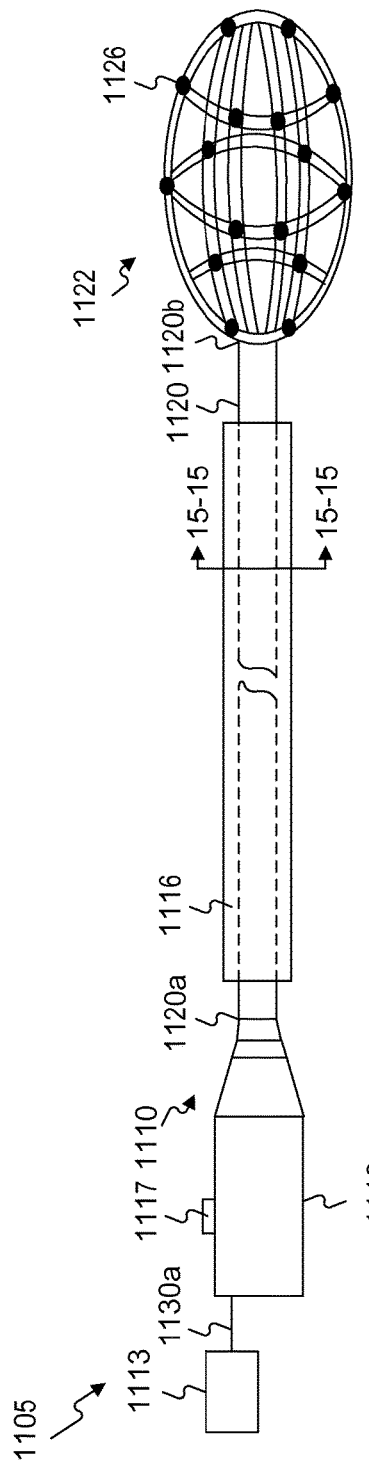
FIG. 14 illustrates another system for treatment of a portion of the gastrointestinal tract, including a medical device, according to an embodiment of the disclosure.

FIG. 14 illustrates an exemplary system 1105 according to another embodiment of the present disclosure. System 1105 has similar components as the system 105 discussed above. In this embodiment, however, at least one external dispenser 1113 may be connected to medical device 1110 via injector 1130. Dispenser 1113 may be a syringe, vial, or other known container configured to retain the material to be injected between and/or into tissue layers of at least one organ, such as the stomach 150 and/or the small intestine 151.

In the exemplary embodiment illustrated in FIG. 14, medical device 1110 includes an elongate member 1120, a handle portion 1118, and an end effector assembly 1122. Elongate member 1120 has a proximal end 1120a and a distal end 1120b. Handle portion 1118 is disposed at proximal end 1120a of elongate member 1120 and includes at least one actuator 1117. End effector assembly 1122 is disposed at distal end 1120b of elongate member 1120. End effector assembly 1122 includes one or more injection units 1126.

Figure 15:
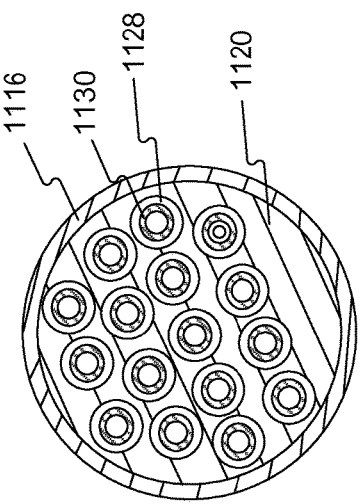
FIG. 15 is a cross-section of the medical device along line 15-15 of FIG. 14.

FIG. 15 is a cross-section of elongate member 1120 along lines 15-15 in FIG. 14. As discussed above, elongate member 1120 may be a solid rod or tube, made from any suitable biocompatible material known to one of ordinary skill in the art having sufficient flexibility to traverse an anatomical lumen such as an esophagus. In this embodiment, elongate member 1120 includes one or more lumens 1128 extending from proximal end 1120a of the elongate member 1120 to distal end 1120b of the elongate member 1120. It is to be understood that lumens 1128 may have any size, cross-sectional area, shape, and/or configuration. Although the depicted embodiment includes sixteen lumens, elongate member 1120 may include a greater or lesser number of lumens 1128. It is to be understood that the number of lumens 1128 may depend on the number of injection units 1126 on end effector assembly 1122.

FIG. 16 depicts a side view of end effector assembly 1122. As shown in FIG. 16, end effector assembly 1122 extends distally from distal end 1120b of elongate member 1120, and includes a plurality of legs 1124a extending from a proximal end 1122a of end effector assembly 1122 to a distal end 1122b of end effector assembly 1122. In some embodiments, end effector assembly 1122 may also include one or more circumferentially extending legs, such as legs 1124b. In this disclosure, descriptions of legs 1124a also pertain to legs 1124b, and vice versa.

End effector assembly 1122 may be made out of the same piece of material as elongate member 1120. Alternatively, end effector assembly 1122 may be fabricated independently by any known means and may be made integral with elongate member 1120 through connection of a proximal end 1122a of the end effector assembly 1122 to a region of elongate member 1120, such as the distal end 1120b of elongate member 1120. The connection of proximal end 1122a of end effector assembly 1120 may be accomplished through any suitable means of fixedly connecting end effector assembly 1122 to elongate member 1120. For example, possible connections may include, but are not limited to welding, soldering, and/or crimping.

End effector assembly 1122 may have any shape and/or configuration and may be any desired dimension that can be received in the stomach 150, small intestine 151, or both organs. In the exemplary embodiment shown in FIG. 16, legs 1124a are configured so that end effector assembly 1122 forms a three-dimensional ovoid in an expanded state. Legs 1124a may be constructed from a material such as, for example, elastic, a shape memory, or super elastic material so that legs 1124a may collapse to have a smaller cross-section in a collapsed state.

Figure 26:
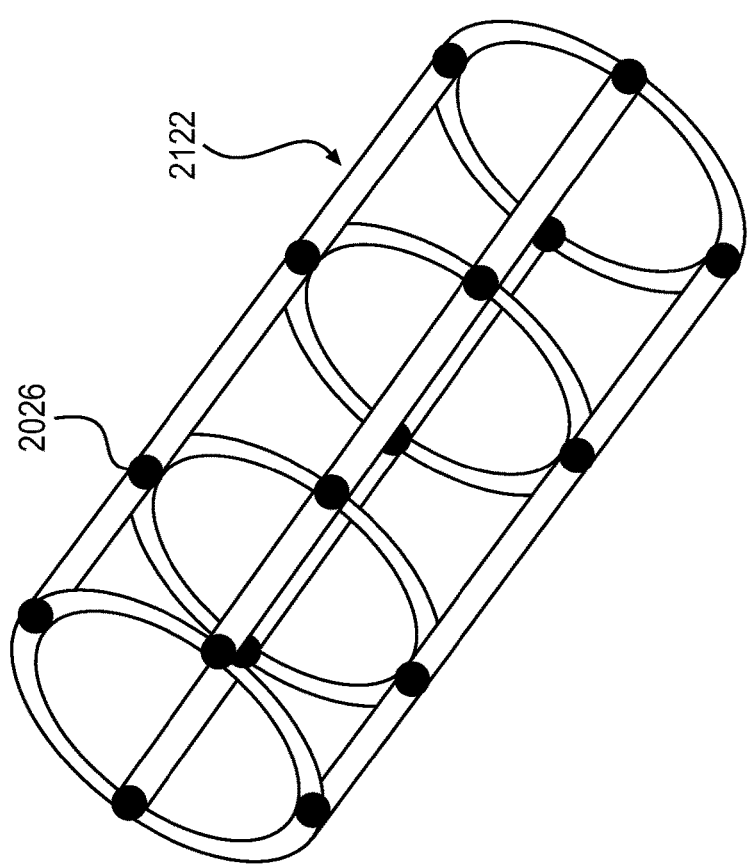
FIG. 26 illustrates an alternative configuration of the end effector assembly of the medical device of FIG. 14, according to an embodiment of the disclosure.

Although FIG. 16, shows that that end effector assembly 1122 comprises six legs 1124a extending from proximal end 1122a of end effector assembly 1122 to distal end 1122b of end effector assembly 1122 (and four circumferential legs 1124b), end effector assembly 1122 may include any number of legs 1124a (or 1124b) having any desired pattern and/or configuration. For example, legs 1124a may form a cylinder, square, semi-circle, rectangle, toroid, or any other suitable shape. In addition, legs 1124a may be any cross-sectional shape known in the art including, but not limited to, circular, square, or ovular. An exemplary cylindrical/toroidal end effector assembly 2122, including suitably arranged injection units 2026, is shown in FIG. 26.

Referring to FIG. 17, each leg 1124a of end effector assembly 1122 includes one or more lumens 1125 located longitudinally therein. Lumens 1125 may have any size, cross-sectional area, shape, and/or configuration. Each lumen 1125 is in communication with a corresponding lumen 1128 of elongate member 1120, and extends from proximal end 1122a of end effector assembly 1122 to an exit aperture 1127 on leg 1124a.

An individual injection unit 1126 is fixed in each exit aperture 1127. In the exemplary embodiment, injection unit 1126 includes a catheter 1132 and an injector 1130 disposed therein. Catheter 1132 may include a proximal end (not shown) terminating proximally of exit aperture 1127 in lumen 1125, and a distal facing surface 1132b flush with, or protruding from, exit aperture 1127. Distal facing surface 1132b may be configured to contact tissue. It is contemplated that in some embodiments, catheter 1132 may move relative to exit aperture 1127. In these embodiments, catheter 1132 may extend proximally through lumen 1125 of legs 1124a and a corresponding lumen 1128, and may be connected to a push and/or pulling mechanism in handle portion 1118.

Referring to FIG. 18, catheter 1132 includes a lumen 1133 extending longitudinally therein. Lumen 1133 may have any size, cross-sectional area, shape, and/or configuration, and may extend from the proximal end (not shown) to an aperture 1133b on distal facing surface 1132b. In the exemplary embodiment, aperture 1133 may have a substantially ovular shape to permit lateral movement of injector 1130. It will be understood, however, that aperture 1133 may have any other size, shape, and/or configuration.

Injector 1130 may be positioned in lumen 1133 of catheter 1132. In particular, injector 1130 may extend proximally from catheter 1132 through lumen 1125 of leg 1124a, a corresponding lumen 1128 of elongate member 1120, and handle portion 1118 (FIG. 14). Injector 1130 may be a conventional needle, including, for example, a microneedle, having a proximal end 1130a, a sharpened distal point 1130c, and a hollow interior. Referring back to FIG. 14, proximal end 1130a may extend proximally of handle portion 1118 for coupling to dispenser 1113. In some embodiments, proximal end 1130a may include a luer fitting or any other fitting to facilitate coupling between proximal end 1130a and dispenser 1113.

Referring to FIGS. 19A-19C, injector 1130 may include a distal portion 1130b. The particular shape, configuration, and/or dimensions of distal portion 1130b of injector 1130 may be selected to penetrate tissue and deliver material at a predetermined depth. In the exemplary embodiment, distal portion 1130b of injector 1130 may have a right angle bend and terminate at distal point 1130c. It will be understood that the bend of distal portion 1130b may be abrupt or curved and may have an angle greater or lesser than 90°. Distal portion 1130b may have any other shape and/or configuration that may penetrate tissue at the desired depth.

Injector 1130 may be operatively connected to the at least one actuator 1117 on handle portion 1118 to move distal portion 1130b of injector 1130 longitudinally relative to lumen 1133 from the retracted configuration in FIG. 19A to the deployed configuration in FIG. 19B. In the deployed configuration, distal portion 1130b of injector 1130 may extend beyond distal facing surface 1132b of catheter 1132 (FIG. 19B). The same actuator 1117 or a different actuator 1117 may be configured to move injector 1130 laterally within lumen 1133 and aperture 1133b between a first position (FIG. 19B) and a second position (FIG. 19C) to facilitate placement of distal point 1130c between tissue layers. In some embodiments, distal portion 1130b of injector 1130 and/or aperture 1133b may include one or more retaining mechanisms to retain distal portion 1130b in the second position during the injection procedure.

A method of treating a target organ 1050, representative of either a stomach or a small intestine in a patient, will now be described. Referring to FIGS. 20A and 20B, medical device 1110 may be inserted into a body lumen (e.g., the esophagus and/or the stomach) of a patient, and may be advanced to the target organ 1050 through outer sheath 1116 (FIG. 20A). Once a distal end of outer sheath 1116 is positioned in the target organ 1050, end effector assembly 1122 may be advanced distally out of outer sheath 1116. This may be achieved by, for example, pushing elongate member 1120 distally relative to outer sheath 1116, or pulling outer sheath 1116 proximally relative to elongate member 1120.

Once end-effector assembly 1122 has been removed from outer sheath 1116, end effector assembly 1122 may be expanded to an expanded configuration (FIG. 20B). In some embodiments, end effector assembly 1122 may self-expand. In other embodiments, an expansion mechanism such as, for example, a balloon may be used to facilitate expansion of end effector assembly 1122. When fully expanded, end effector assembly 1122 may have a shape mimicking an interior of the target organ 1050, positioning each injection unit 1126 adjacent an interior surface of a wall 1040 of the organ.

Figures 21A, 21B, 21C:
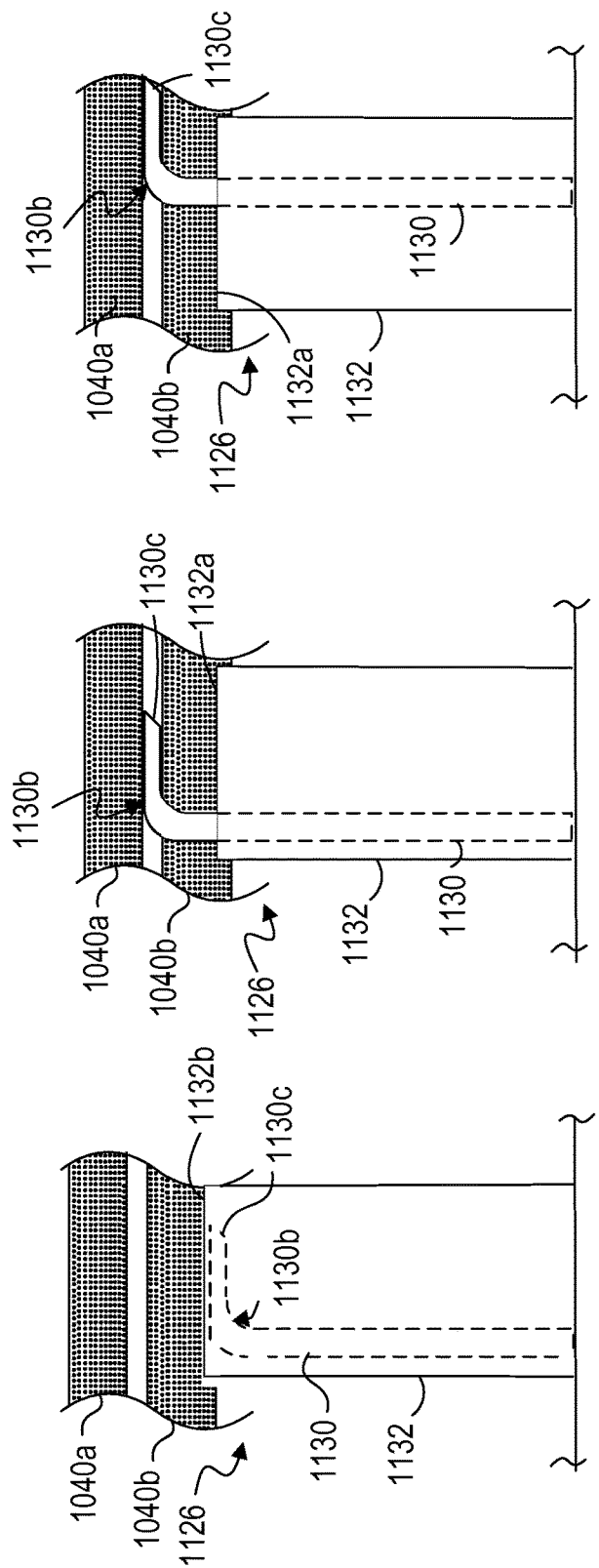
FIG. 21A illustrates an individual injection unit contacting a wall of a portion of the gastrointestinal tract, according to an embodiment of the disclosure.
FIG. 21B illustrates an injector being deployed from a catheter of the injection unit with the injector in a first position, according to an embodiment of the disclosure.
FIG. 21C illustrates the injector of FIG. 21B in a second position, according to an embodiment of the disclosure.

The procedure continues with the physician inserting distal portion 1130a of each injector 1130 into the wall 1040. In particular, the physician may engage the at least one actuator 1117 on handle portion 1118 to move injectors 1130 relative to lumens 1128 in elongate member 1120, lumens 1125 in legs 1124a (or legs 1124b), and lumens 1133 in catheters 1132 in order to advance distal portion 1130b of injectors 1130 from a retracted position within lumen 1133 of catheter 1132 to a deployed position distal to a distal facing surface 1132b of catheter 1132 (FIGS. 21A and 21B).

As distal portion 1130b extends out of aperture 1133b, distal point 1130c may be configured to penetrate tissue. As discussed in the embodiment described above, it may be desirable to penetrate tissue and inject material at a predetermined depth. The penetration depth may be monitored/adjusted in a number of ways. For example, distal portion 1130b of injector 1130 may be shaped and/or dimensioned to piece the wall 1040 to a desired depth so that material may be delivered at the predetermined depth (e.g., between layers forming at least a portion of the wall 1040, similar to the depiction in FIG. 7E). Additionally and/or alternatively, injector 1130 may be provided with radiopaque markers that can be visualized as distal portion 1130b is penetrating tissue. In further embodiments, actuator 1117 may enable operator to advance injectors 1130 simultaneously or individually in known increments.

Once injectors 1130 are in the deployed position, the same actuator 1117 or a different actuator 1117 may be configured to drive distal portion 1130b of each injector 1130 laterally in apertures 1133b. Lateral movement of injector 1130 between a first position shown in FIG. 21B and a second position shown in FIG. 21C may facilitate positioning of distal point 1130c between layer 1040b and layer 1040a of wall 1040. Material may then be injected from dispenser 1113 through the proximal end 1130a of each injector 1130 to deliver the material between and/or into tissue layers. For example, the material may be injected between the of smooth muscle and the myenteric plexus of a portion of the wall of the small intestine.

In some embodiments, the physician may uniformly treat the target organ 1050 by simultaneously delivering material through all of the injection units 1126. In other embodiments, the physician may selectively deliver material through one or more specific injection units 1126 to treat areas of the target organ 1050 individually. In these embodiments, medical device 1110 may include a sensing element to detect a certain area and transmit the data via a cable or wirelessly to the physician.

As in the embodiments described above, the material may be delivered between a layer 1040b and a layer 1040a to separate the two layers. In additional and/or alternative embodiments, the medical device may include a suction lumen positioned at a distal end 1120b of elongate member 1120, a distal end 1122b of end effector assembly 1122, and/or in each catheter 1132 to assist in the lifting of tissue layers through suction to separate the two tissue layers. The suction procedure is followed with fluid/material insertion between the layers.

Alternative non-limiting examples of end effector assemblies having various shapes and/or distal configurations are shown in FIGS. 22A-22E. FIGS. 22A and 22D depict end effector assemblies having wire configurations. In particular, end effector assembly 1522a, as shown in FIG. 22A, may have a substantially linear configuration. A single end effector unit 1126 may be disposed at a distal end of end effector assembly 1522a. In another embodiment, end effector assembly 1522d, as shown in FIG. 22D, may have a helical configuration preferably tapering from a larger diameter at a distalmost end thereof to a smaller diameter proximally of the distalmost end thereof. A kink may be disposed adjacent a proximal end of end effector assembly 1522d. FIG. 22C depicts an end effector assembly 1522c having a plurality of legs curving away from a longitudinal axis of end effector assembly 1522c. FIGS. 22B and 22E depict end effector assemblies having a mesh configuration. In particular, end effector assembly 1522b, as shown in FIG. 22B, may have a circular shape. And in yet another embodiment, end effector assembly 1522e, as shown in FIG. 22E, may have a semi-circular shape. End effector assemblies 1522c and 1522e may be additionally planar, concave, or convex.

Alternative embodiments of injection units will now be described. It will be noted that at least certain aspects of the embodiments discussed below may be combined with other aspects of the embodiments discussed above. For example, one or more of the following injection units may be provided on one of the end effector assemblies discussed above to position the injection units within the target organ 1050.

FIGS. 23A-23C illustrate an injection unit 1226. Injection unit 1226 includes a catheter 1232 and an injector 1230. Catheter 1232 may have a proximal end (not shown), a distal end 1232b, and a lumen 1233 extending therethrough. In the exemplary embodiment, distal end 1232b of catheter 1232 may be wedge shaped. It is contemplated that distal end 1232b may be sharpened to facilitate insertion into tissue.

Lumen 1233 may terminate at an aperture 1233b on a distal facing surface 1232c of catheter 1232. Distal facing surface 1232c may include one or more features to drive injector 1230 to a desired position and orient injector 1230 relative to catheter 1232. For example, distal facing surface 1232c may include a ramp 1232d adjacent aperture 1233b. Ramp 1232d may be shaped to drive injector 1230 from a first position on one end (side) of distal end 1232b of catheter 1232 to a second position on an opposing end (side) of distal end 1232b of catheter 1232. In particular, ramp 1232 may be disposed in a plane that is not perpendicular to a longitudinal axis of catheter 1232 (FIG. 23A). Furthermore, ramp 1232d may be sized and shaped to interact with one or more aligning members 1235 on injector 1230 to orient injector 1230 relative to catheter 1232. For example, the width of ramp 1232d may be sized to receive an aligning member 1235 and to prevent rotation of the aligning member 1235 and injector 1230.

Figure 24A:
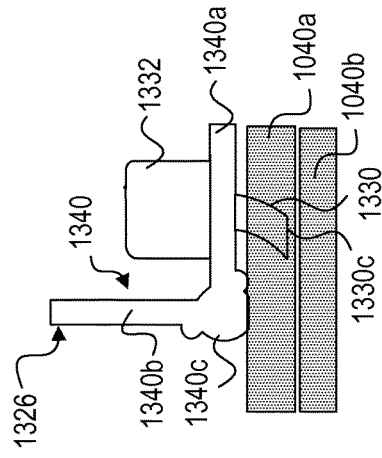
FIG. 24A is schematic view of an injection unit, in accordance with an embodiment of the disclosure.
Figure 24B:
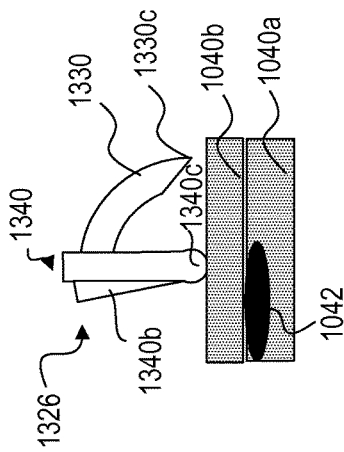
FIG. 24B is a schematic view of the injection unit of FIG. 24A, with an injector inserted into tissue of a wall of a portion of the gastrointestinal tract, according to an embodiment of the disclosure.
Figure 24C:
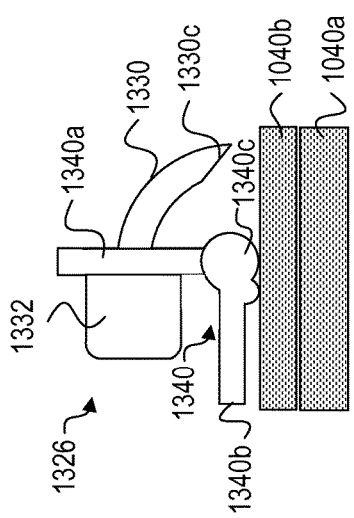
FIG. 24C is a schematic view of the injection unit of FIG. 24A, with a collapsed dispenser, according to an embodiment of the disclosure.
Figure 24D:
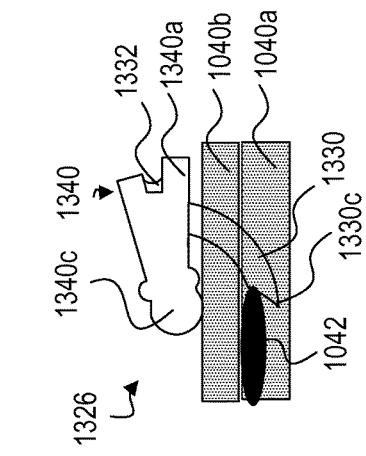
FIG. 24D is a schematic view of the injection unit of FIG. 24A, with the injector retracted from the tissue, according to an embodiment of the disclosure.

FIGS. 24A-24C illustrate an injection unit 1326 in accordance with another embodiment of the disclosure. Injection unit 1326 may include a frame 1340 having a first arm 1340a and a second arm 1340b pivotably connected to the first arm 1340a via a pivot 1340c. An injector 1330 may be provided on first arm 1340a. In particular, injector 1330 may be fixed to a surface of first arm 1340a and may extend in a direction generally perpendicular to first arm 1340. Frame 1340 may be a positioning mechanism configured to position injector 1330 adjacent tissue and facilitate insertion of injector 1330 into tissue.

In this embodiment, injector 1330 may be a curved needle, including, for example, a micro-needle, having a sharpened distal point 1330c and a hollow interior. Injector 1330 may be sized to penetrate tissue and inject material at a predetermined depth. It is understood that injector 1330 may have any other size and/or configuration to penetrate tissue at the predetermined depth.

A dispenser 1332 may be mounted on first arm 1340a opposite to injector 1330. Dispenser 1332 may be in fluid communication with injector 1330 via an aperture (not shown) in first arm 1340a. In this embodiment, dispenser 1332 may be an elastomeric fluid container retaining material to be injected between two tissue layers. Dispenser 1232 may have an impermeable membrane or a collapsible wall configured to collapse on application of sufficient force by an injection mechanism such as, for example, second arm 1340b. As dispenser collapses, the material may be introduced into injector 1330.

Injection unit 1326 may be introduced into the target organ 1050 and positioned adjacent the organ wall 1040 using the procedures discussed above. Injection unit 1326 may be placed adjacent the organ wall 1040 with second arm 1340b parallel to the layer 1040a and layer 1040b of organ wall 1040. In order to insert injector 1330 into tissue, frame 1340 may be rotated, so that second arm 1340b is generally perpendicular to the tissue. Any known actuation mechanism, such as an electrical actuator or linear actuator, may be attached to frame 1340 and may be configured to apply sufficient force to rotate frame 1340. As frame 1340 rotates, distal point 1330c of injector 1330 may be inserted into the tissue.

The procedure may continue by collapsing dispenser 1332. For example, the same actuation mechanism or a different actuation mechanism may apply a force to second arm 1340b to pivot second arm 1340b relative to first arm 1340a about pivot 1340c. As second arm 1340b pivots towards the first arm 1340a, second arm 1340b may apply sufficient force to collapse dispenser 1332. In this manner, material 1042 may be injected into injector 1330 for delivery between tissue layers. Injector 1330 may be removed by rotating first arm 1340a, so that first arm 1340a and second arm 1340b are generally perpendicular to the tissue.

FIGS. 25A and 25B illustrate an injection unit 1426 in accordance with another embodiment of the disclosure. In this embodiment, injection unit 1426 includes a housing 1440 having a closed top 1450, an open bottom 1460, and a space 1470 extending therebetween. The closed top 1450 may be closed by, for example, a cap. In some embodiments, the cap may include a breathable membrane. The open bottom 1460 may be configured to be oriented towards tissue and contact tissue.

A first magnetic disk 1444 may be disposed in space 1470, and may be configured to move relative to housing 1440 between the closed top 1450 and open bottom 1460. The first magnetic disk 1444 may sealingly engage the inner walls of housing 1440. For example, first magnetic disk 1444 may have radial seals, such as, for example an O-ring or a lip seal, to engage housing 1440. A second magnetic disk 1442 may be disposed between the first magnetic disk 1444 and the open bottom 1460. Second magnetic disk 1442 may have similar seals.

An injector 1430 may be fixed to second magnetic disk 1442. In particular, a proximal end 1430a of injector 1430 may extend through an aperture (not shown) in second magnetic disk 1442 and may be fixed to the aperture. In this embodiment, injector 1430 may be a cylindrical needle, such as, for example, a micro-needle, having a sharpened distal point 1430c and a hollow interior. Injector 1430 may be sized to penetrate tissue and inject material at a predetermined depth. It is understood that injector 1430 may have any other size and/or configuration to penetrate tissue.

A dispenser 1432 may be disposed between the first magnetic disk 1444 and the second magnetic disk 1442. In this embodiment, dispenser 1432 may be a collapsible dispenser retaining fluid in, for example, a collapsible, impermeable membrane. The membrane may be configured to collapse and rupture on application of sufficient force to inject the material into proximal end 1430a of injector 1430.

Housing 1440 may further include coil windings 1446 disposed on an outer surface of housing 1440. Coil windings 1446 may attach to an electrical wire (not shown) that may extend proximally through a medical device to a source of electricity. In operation, housing 1440, first magnetic disk 1444, second magnetic disk 1442, and coil windings 1446, together, may be a positioning mechanism configured to position injector 1430 adjacent tissue and facilitate insertion of injector 1330 into tissue. In particular, current may pass through the coil windings 1446 inducing an electrical field whose electromotive force may be used to drive first magnetic disk 1444 and second magnetic disk 1442 downward. The force may be sufficient to insert injector 1430 into the adjacent tissue.

After injector 1430 has been inserted into tissue, the electromotive force may continue to drive the first magnetic disk 1444 downward. First magnetic disk 1444 may act as an injection mechanism by applying sufficient pressure on dispenser 1432 to rupture dispenser 1432 disposed between the first magnetic disk 1444 and the second magnetic disk 1442. In this manner, material may be injected into injector 1430 for delivery between two tissue layers.

The same deployment may be accomplished with an electrical coil and a spring recoil. In particular, current may be applied to the coil windings of the injection unit in only one direction to insert injector into tissue and inject material between the two tissue layers. The recoil spring (placed between second magnetic disk 1442 and open bottom 1460) may then retract injector 1430. In another embodiment, deployment may be accomplished with a compressed fluid and a spring recoil. In this embodiment, the compressed fluid, applied to first magnetic disk 1444, may be configured to apply sufficient force to deploy injector 1430 and inject the material. As in the embodiment described above, the recoil spring may retract injector 1430 once the fluid pressure is relieved.

Other injection units are contemplated. For example, in other embodiments, each of the one or more injection units may have a micro-needle array in place of a single injector. In this manner, the injection unit may target a wider area of tissue within the target organ 1050. In additional and/or alternative embodiments, the material may be dispersed through the injector (or needle array device) onto tissue adjacent the injection units without perforating the wall 1040. This procedure may be performed for a set duration at varying amplitudes to increase the permeability of one or more layers forming the wall 1040.

In some embodiments, the fluid dispenser 1432 does not rupture, but rather fluid is releasable upon application of pressure which forces fluid through pores in the wall of the dispenser. The pores may be elastic or nonelastic, and may be holes, slots, or slits. Alternatively, the fluid dispenser 1432 may remain sealed and the needle includes pores, slots, holes, or slits that open with increased pressure and convey fluid from the dispenser to the tissue.

Figure 27:
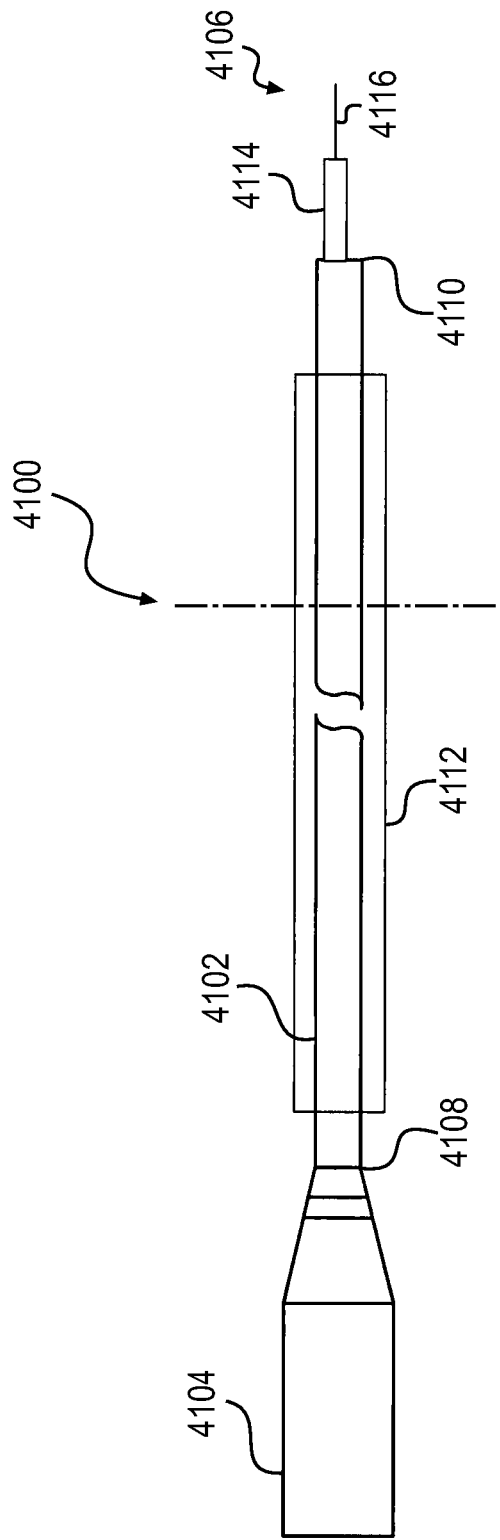
FIG. 27 illustrates another exemplary medical device for injecting a substance into a wall portion of the gastrointestinal tract, according to an embodiment of the disclosure.

FIG. 27 illustrates an exemplary medical device 4100 for injecting material between and/or into tissue layers, according to an embodiment of the present disclosure. Medical device 4100 includes an elongate tube 4102, a handle 4104, and an injector device 4106. Elongate tube 4102 has a proximal end 4108 and a distal end 4110, those terms referring to positions or directions nearer to or farther from the user, respectively. Elongate tube 4102 may include one or more lumens. In some embodiments, the lumen(s) of elongate tube 4102 may be used to pass one or more tools to a target site within a patient's body. Such tools may include, e.g., biopsy devices, snares, suture needles, laser fibers, or suitable imaging devices. In addition, elongate tube 4102 may include integrally-formed illumination and imaging devices.

Elongate tube 4102 extends from handle 4104 to injector device 4106 and advances injector device 4106 into an operating position, as discussed below. Elongate tube 4102 is hollow, with cross-sectional configuration adapted to be received in one or more portions of the gastrointestinal tract. In the illustrated embodiment, elongate tube 4102 includes a generally circular cross-section, with a generally circular hollow interior opening. Further, elongate tube 4102 is also adapted for flexible steering within bodily lumens, as understood in the art. In particular, distal end 4110 of elongate tube 4102 may be selectively steerable.

Elongate tube 4102 may be formed from any suitable material having sufficient flexibility to traverse body cavities and tracts. Suitable materials may include synthetic plastics and polymers. Alternatively, materials, such as, stainless steel or the like, including shape memory alloys such as nitinol, have proved particularly suitable for such applications. The degree of flexibility imparted to elongate tube 4102 can vary based on the particular application, ranging from highly flexible tubes adapted to be highly maneuverable, to tubes that are substantially rigid.

Medical device 4100 may be enclosed in an outer sheath 4112, which may surround elongate tube 4102 and injector device 4106 from the flexible tube's proximal end to the injector device's distal end. Sheath 4112 preferably has the same cross-sectional shape as elongate tube 4102 and fully covers elongate tube 4102 and/or injector device 4106. In this state, medical device 4100 may be inserted into a body cavity or surgically advanced to the desired site. When medical device 4100 is positioned at the desired location, sheath 4112 may be pulled proximally or elongate tube 4102 may be pushed distally so that injector device 4106 extends out of the sheath's distal end into an operating state. The injector device's actuation described here may be carried out by any actuation mechanism known now or that may be developed in the future without departing from the scope of the present disclosure. For example, a pulling or pushing mechanism may be incorporated in handle 4104 allowing the physician to easily deploy injector device 4106 when required. For purposes of this disclosure, sheath 4112 may be formed of material such as polyamide, polyurethane, rubber, or any other suitable material.

Moreover, sheath 4112 may include one or more lumens for passing suitable tools to a target site within a patient's body. These tools may include, e.g., biopsy devices, snares, resection devices, suture needles, imaging devices, and/or illumination devices. In some embodiments, sheath 4112 may include integrally-formed illumination and imaging devices.

The injector device 4106 of the illustrated embodiment takes the form of a conventional needle, having a sharpened distal point and hollow interior. This device may be adapted for attachment to elongate tube 4102 by conventional means, such as a screw attachment. If detachable, injector device 4106 may be disposable. Alternatively, this device can be formed integrally with the remainder of the instrument. As illustrated, medical device 4100 employs a single injector device 4106, but it will be understood that multiple devices could be employed. For example, one embodiment could include multiple elongate tubes 4102 carried within a sheath 4112, each elongate tube 4102 having its own injector device 4106 and injector 4116, allowing injection at multiple locations, as desired. As another example, one embodiment could include multiple elongate tubes 4102a-4102d similar to the elongate tube 4012, each forming a part of a device similar to the device 4100, and carried within a sheath or endoscope (see FIG. 30). Those in the art will understand that a range of alternatives could be brought to bear for alternate implementations of injector device 4106. In other embodiments, for example, a single injector device 4106 may include a plurality of injectors 4116. For example, the device of FIG. 27 may include two or more injectors 4116 instead of the single injector 4116 shown.

The medical device 4100 may include an expandable member for securing the injector device 4106 near an organ wall. For example, the expandable member may be an inflatable balloon, which may be inflated once the injector device 4106 is extended out of the elongate tube 4102 for fluid insertion. As known in the art, any other suitable expandable member, including, e.g., a mechanical cage or foam, may be employed for securing the medical device 4100 near the organ wall.

Additionally, injector 4116 disclosed here may include mechanical or electrical injectors. Different types of injectors 4116 are well known in the art and will not be described in detail here. The fluid to be injected may be carried in a fluid dispenser (not shown). That dispenser may be a part of the injector 4116 or may be present at the proximal end of the elongate tube 4102 near handle 4104. As known in the art, the fluid dispenser may be operated manually or under computer control to deliver the fluid at the targeted area.

In some embodiments, the medical device may include a suction device at a distal end to assist in the lifting of one or more layers of the organ wall by suction procedure to separate the layers. The suction procedure is followed with fluid insertion in between the layers. The distal end of the medical device may also include integrated illumination and/or visualization optics (i.e., camera).

In addition, a portion of the medical device 4100 may include a coating. In one embodiment of the present disclosure, the medical device 4100 may be coated with an antibacterial material to inhibit bacterial growth on the surface of the medical device 4100. Alternatively, the medical device 4100 may be coated with a lubricious coating to facilitate convenient insertion into the body, and through one or more body passages, including, for example, the esophagus, stomach, and/or small intestine. In some embodiments, medical device 4100 may include radiopaque or sonoreflective markers to locate the medical device 4100 inside the body lumens.

Figure 28:
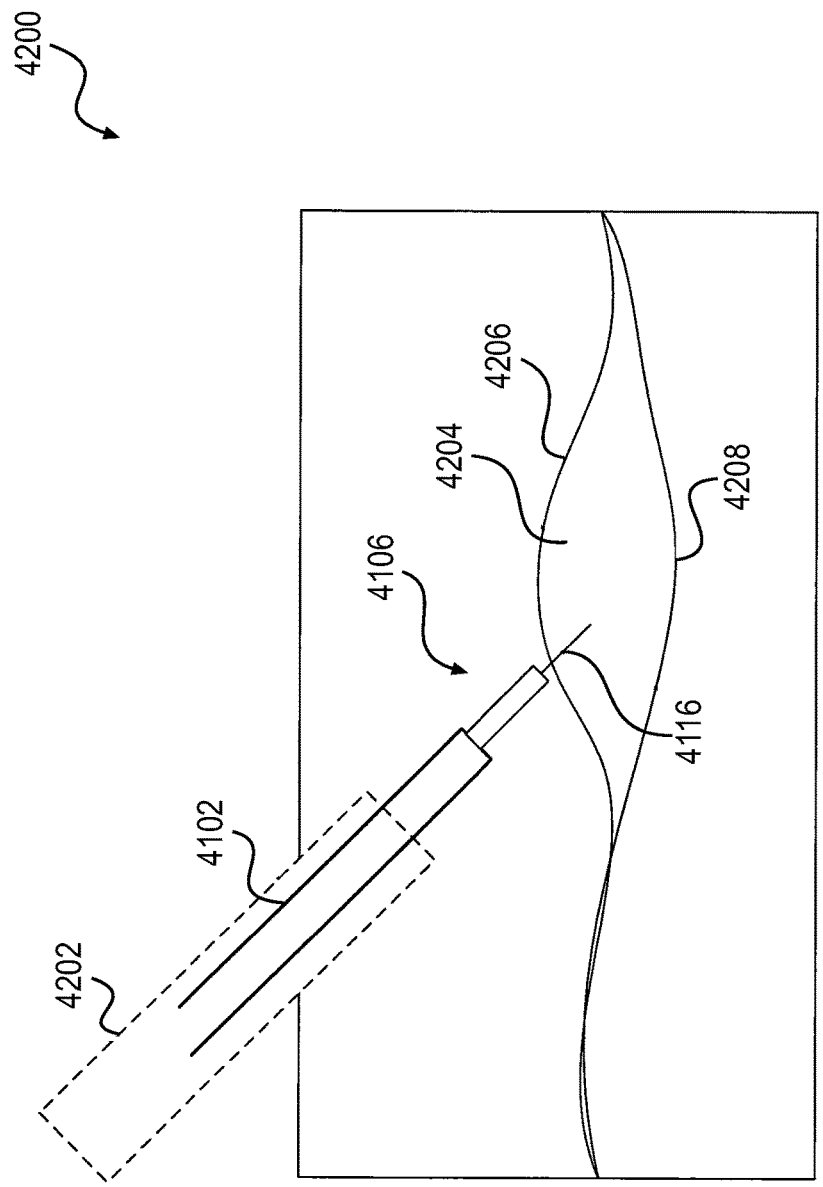
FIG. 28 is a schematic view of an exemplary method for injecting a substance into a wall portion of the gastrointestinal tract, utilizing the medical device of FIG. 27, according to an embodiment of the disclosure.

FIG. 28 is a schematic view of an exemplary method for separating layers in regions of the organ wall, illustrating an embodiment of the present disclosure. It will be understood, the disclosed method will be described as applied to treatment of the small intestine and/or the stomach. Those of skill in the art, however, will readily recognize that the principles of the disclosed embodiments may have utility relative to any organ within a patient's body. It will be further noted that both FIG. 28 and the discussion that follows below use like reference numbers to refer to elements of the medical device 4100 shown in FIG. 27. Specifically, the illustrated embodiment of the present disclosure employs a medical device 4200, which may be any suitable endoscopic device, such as a guide catheter.

The method illustrated in FIG. 28 includes injecting an inert fluid or gel between a layer 4208 (e.g., the myenteric plexus of the small intestine wall) and a layer 4206 (e.g., the layer of smooth muscle of the small intestine wall). This method calls for inserting catheter 4202 into the esophagus and stomach, extending the distal end of elongate tube 4102 into the small intestine. Using appropriate visualization means, the physician identifies the site of interest 4204, where the injection is to occur. As suggested above, the site of interest may be a previously or simultaneously identified location exhibiting abnormal activity or morphology. Then, injector device 4106 is extended distally from elongate tube 4102, exposing injector 4116. This configuration of medical device 4200 may be referred to as an "operating state" in which the device is prepared to perform the injection. Previously, injector device 4106 and injector 4116 are retracted within elongate tube 4102, permitting elongate tube 4102 to be advanced through the esophagus and stomach and into the small intestine without damaging adjacent tissues. The process of extending injector device 4106 into the operating state is well known in the art and need not be discussed here.

The procedure continues with the physician advancing injector 4116 to pierce the layer 4206 employing either manual control or a visualizing techniques. The layer depth may be monitored by a number of ways. For example, the injection needle may be a single predetermined length. Alternatively, the needle may be provided with radiopaque markers that can be visualized as the needle is penetrating tissue. In another embodiment, the device may be provided with a ratchet-like advancing mechanism, wherein the operator may be able to selectively advance the needle in known increments.

Once the distal tip of injector 4116 reaches a site of interest 4204, medical device 4200 is actuated to inject a requisite amount of material between the layer 4206 and the layer 4208. The injected material may include any of the injectable materials described above. As shown in FIG. 28, the material may serve to separate and maintain the two layers 4206 and 4208. After the injection is complete, the physician may retract injector device 4106 to its non-operating state within catheter 4202. The physician can then move the distal tip of medical device 4200 to a second site of interest and perform a further injection, or medical device 4200 can be withdrawn from the patient's body.

In some embodiments, the medical device 4200 may include a suction device to assist in lifting the layer 4208.

The description above contemplates a primarily manual operation of the disclosed method. As known in the art, however, a number of automation techniques may be applied to improve control and accuracy of the process. For example, the exact positioning and depth of penetration may be monitored by appropriate visualization technology, or the penetration itself can be carried out under computer control.

Figure 29:
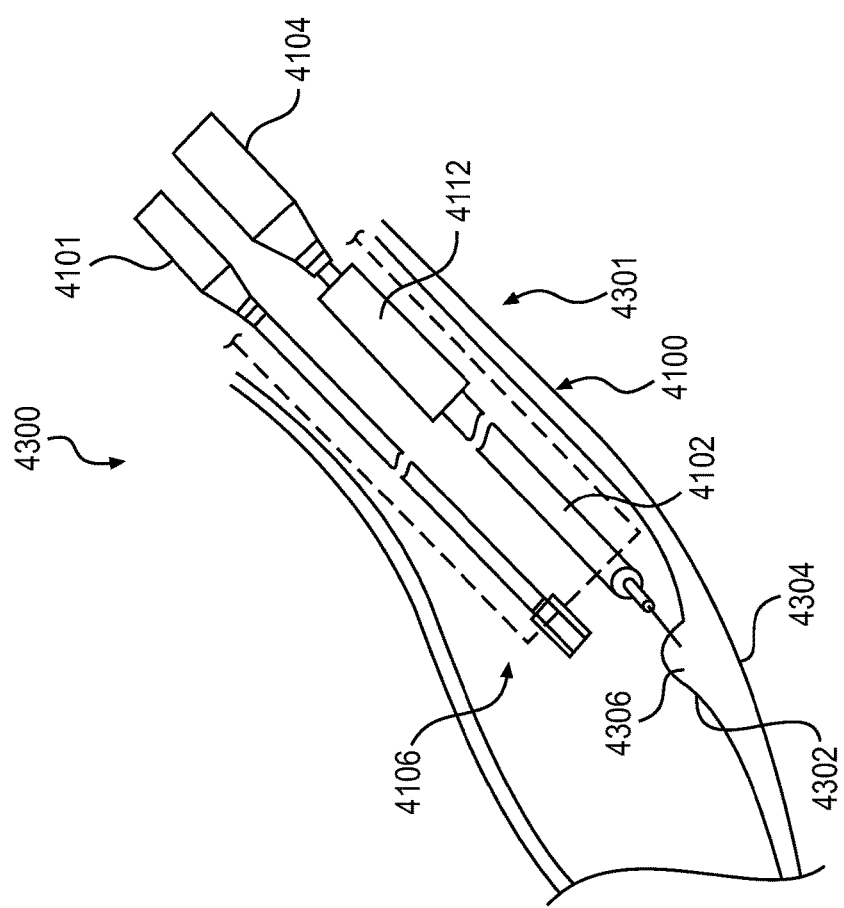
FIG. 29 is a schematic view of an exemplary method for treating a portion of the gastrointestinal tract, utilizing the medical device of FIG. 27, according to an embodiment of the disclosure.

FIG. 29 illustrates an approach to advancing the distal tip of medical device 4100 into position to perform the required injection. As illustrated, surgical techniques are employed to introduce a device, such as an endoscope 4301 into a target area (e.g., an organ like the stomach or the small intestine) and bring the distal portion of endoscope 4301 into a selected position adjacent an organ wall. Alternative surgical approaches to position endoscope 4301 adjacent the organ wall will be apparent to those skilled in the art. In addition, the contemplated method may be utilized with other organs throughout a patient's body.

Once in position, injector 4116 may be actuated by handle 4104 to pierce the organ wall. In another embodiment, suction may be applied to pull tissue towards the device or make the tissue taut for piercing the organ wall. Injector 4116 pierces the organ wall and traverses the layer 4302 to a desired depth, operating under manual or computer control. The injected fluid 4306 physically separates the layer 4302 and the layer 4304. The fluid insertion between the layers 4304 and 4302 may be performed at multiple locations of the organ wall. It is also contemplated that fluid insertion may be performed in locations of the organ wall of one organ, and then performed in locations of the organ wall of a different organ. Further, the procedure may be repeated periodically depending upon the chemical nature of injected fluid 4306. As would be understood by a person of ordinary skill in the art, any other method for dispensing fluids may be employed for delivering fluid to the injector 4116. Once the layer 4304 and the layer 4302 are physically separated, the injector device 4106 is removed from the target area.

A control mechanism may operate injector 4116 either manually or automatically. For example, a physician may monitor the treatment location, the depth of the layers 4302 and 4304, and amount of compound to be injected between the layers 4302 and 4304 in the targeted area, via an endoscope 4301. Alternatively, the control mechanism may automatically insert the medical device 4100 into a human body, penetrating the wall to deliver liquid or gel under computer control, as would be understood by a person skilled in the art. In automated embodiments, parameters may be provided as a set of instructions to a processor, which automatically controls the injector 4116 to pierce the wall to a desired depth and injects the requisite amount of compound 4306 to the wall's targeted location.

It is further contemplated that one or more of the above-described injection units (described in relation to FIGS. 1-30), may inject material approximately 1-4 millimeters below a surface of an organ wall. The depth of injection may be set within that range, and even outside of that range, depending on patient anatomy. Further, it is also contemplated that one or more of the above-described end effector assemblies (described in relation to FIGS. 1-30), that is configured for injecting in multiple sites, may include between 10 and 60 injection units. For example, one or more of the above-described end effector assemblies may include between 10 and 20 injection units for injecting material into the small intestine, and/or 20-40 injection units for injecting material into the stomach. It should be understood, however, that the number of injection units may be greater or lesser depending on a patient's anatomy. It is even contemplated that there may be 100 injection units. Those injection units may be configured to inject smaller volumes of material with many closely-spaced injections.

Aspects of the systems and methods described in U.S. Provisional Patent Application No. 61/535,710, filed Sep. 16, 2011, U.S. Provisional Patent Application No. 61/677,590, filed Jul. 31, 2012, U.S. Provisional Patent Application No. 61/798,618, filed Mar. 16, 2013, U.S. Provisional Patent Application No. 61/799,260, filed Mar. 15, 2013, and U.S. Nonprovisional patent application Ser. No. 13/599,916, filed Aug. 30, 2012, are all herein incorporated by reference in their entirety.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be apparent that the medical device of the present disclosure may be used to carry out a variety of medical or non-medical procedures, including surgical and diagnostic procedures in a wide variety of bodily locations. In addition, at least certain aspects of the aforementioned embodiments may be combined with other aspects of the embodiments, or removed without departing from the scope of the disclosure.

What is claimed is:

1. A treatment method, comprising:
   treating a wall of a portion of a gastrointestinal tract of a patient, wherein treating the wall includes:
   positioning one or more injection units adjacent to the wall, wherein positioning the one or more injection units includes expanding a first expandable member to move the one or more injection units toward the wall, with the one or more injection units mounted on an interior surface of the first expandable member; and
   affecting at least one of movement of gastrointestinal tract contents through the gastrointestinal tract and absorption of gastrointestinal tract contents by the gastrointestinal tract, by injecting material into the wall using the one or more injection units, wherein injecting the material includes injecting the material between layers forming at least a portion of the wall, and wherein injecting the material into the wall includes expanding a second expandable member to bring an exterior surface of the second expandable member into engagement with the one or more injection units.

2. The treatment method of claim 1, wherein engagement of the second expandable member with the one or more injection units compresses the one or more injection units.

3. The treatment method of claim 1, wherein the one or more injection units include a needle, a reservoir containing the material, and a pocket defining a cavity for receiving the needle.

4. The treatment method of claim 3, wherein the needle is coupled to the reservoir, the needle and the reservoir are coupled to the interior surface of the first expandable member by the pocket, and injecting the material includes moving the needle from a first position contained within the cavity to a second position extending out of the cavity by expanding the first expandable member to decrease a depth of the pocket.

5. The treatment method of claim 3, wherein the one or more injection units include a membrane between the needle and the reservoir, and injecting the material includes rupturing the membrane.

6. The treatment method of claim 1, wherein injecting the material between the layers separates the layers, and the separation inhibits at least one of movement of the wall and absorption of one or more nutrients in the gastrointestinal tract contents by the gastrointestinal tract.

7. The treatment method of claim 6, wherein injecting the material between the layers forms a barrier between the layers.

8. A treatment method, comprising:
   treating a wall of a portion of a gastrointestinal tract of a patient, wherein treating the wall includes:
   inserting one or more injection units of a medical device through an anatomical passage forming at least a portion of the gastrointestinal tract; and
   positioning the one or more injection units adjacent to the wall, wherein positioning the one or more injection units includes expanding an expandable member to move the one or more injection units toward the wall, and the one or more injection units are mounted on an interior surface of the expandable member, and wherein the expandable member is a first expandable member, and injecting the material includes expanding a second expandable member to bring an exterior surface of the second expandable member into engagement with the one or more injection units to compress the one or more injection units; and
   controlling at least one of movement of gastrointestinal tract contents through the gastrointestinal tract and absorption of gastrointestinal tract contents by the gastrointestinal tract, by injecting material into the wall using the one or more injection units, wherein injecting the material includes injecting the material between layers forming at least a portion of the wall.

9. The treatment method of claim 8, wherein injecting the material includes expanding the first expandable member to cause the one or more injection units to penetrate the first expandable member.

10. The treatment method of claim 8, wherein the one or more injection units include a needle, and injecting the material includes penetrating the wall with the needle to a depth at which injection of the material into the wall separates the layers.

* * * * *